United States Patent
First et al.

(10) Patent No.: US 11,045,396 B2
(45) Date of Patent: Jun. 29, 2021

(54) DEVICES AND METHODS FOR THE SUPPLEMENTATION OF A NUTRITIONAL FORMULA

(71) Applicant: Alcresta Therapeutics, Inc., Newton, MA (US)

(72) Inventors: Eric First, Morristown, NJ (US); David Widom, Long Valley, NJ (US)

(73) Assignee: Alcresta Therapeutics, Inc., Newton, MA (US)

( * ) Notice: Subject to any disclaimer, the term of this patent is extended or adjusted under 35 U.S.C. 154(b) by 195 days.

(21) Appl. No.: 15/998,410

(22) Filed: Aug. 15, 2018

(65) Prior Publication Data

US 2019/0053987 A1     Feb. 21, 2019

Related U.S. Application Data

(60) Provisional application No. 62/546,817, filed on Aug. 17, 2017.

(51) Int. Cl.
    *A61J 9/00*        (2006.01)
    *A61J 1/20*        (2006.01)
    (Continued)

(52) U.S. Cl.
CPC ............. *A61J 9/005* (2013.01); *A23L 33/115* (2016.08); *A61J 1/2003* (2015.05); *A61J 1/2089* (2013.01); *A61J 1/2093* (2013.01); *A61J 15/0003* (2013.01); *A61J 15/0026* (2013.01); *A23L 33/00* (2016.08); *A61J 1/067* (2013.01); *A61J 7/0053* (2013.01); *A61K 9/00* (2013.01)

(58) Field of Classification Search
CPC ...... A61J 9/005; A61J 1/2003; A61J 15/0003; A61J 15/0026; A61J 1/2089; A61J 1/2093; A61J 1/067; A61J 7/0053; A23L 33/115; A61K 9/00
USPC ....................................................... 435/289.1
See application file for complete search history.

(56) References Cited

U.S. PATENT DOCUMENTS

| 4,629,742 A | 12/1986 | Brady et al. |
| 4,944,944 A | 7/1990 | Tang et al. |

(Continued)

FOREIGN PATENT DOCUMENTS

| CN | 101573048 A | 11/2004 |
| CN | 101068565 A | 11/2007 |

(Continued)

OTHER PUBLICATIONS

Abbott Laboratories (2009) "ProSure® Therapeutic Nutrition for People with Cancer" Product Monograph (48 pages).

(Continued)

*Primary Examiner* — Michael L Hobbs
*Assistant Examiner* — Lenora A Abel
(74) *Attorney, Agent, or Firm* — Bookoff McAndrews, PLLC

(57) ABSTRACT

Exemplary embodiments of the disclosure may be drawn to a device having a vessel configured to contain a source of lipids and a chamber fluidly connected to an outlet of the vessel. The chamber may contain immobilized lipase positioned within a flow path in the chamber along which the lipids flow when released from the vessel into the chamber. The device may also include an outlet through which the lipids flow after passing through the chamber.

23 Claims, 14 Drawing Sheets

(51) Int. Cl.
*A23L 33/115* (2016.01)
*A61J 15/00* (2006.01)
*A61J 1/06* (2006.01)
*A61J 7/00* (2006.01)
*A23L 33/00* (2016.01)
*A61K 9/00* (2006.01)

(56) References Cited

U.S. PATENT DOCUMENTS

| | | | |
|---|---|---|---|
| 5,010,004 | A | 4/1991 | Kosugi et al. |
| 5,902,617 | A | 5/1999 | Pabst |
| 6,346,216 | B1 | 2/2002 | Kent |
| 6,541,606 | B2 | 4/2003 | Margolin et al. |
| 6,635,222 | B2 | 10/2003 | Kent |
| 6,749,851 | B2 | 6/2004 | Mann et al. |
| 8,361,763 | B2 | 1/2013 | Dayton |
| 8,404,470 | B2 | 3/2013 | Thum et al. |
| 8,754,126 | B2 | 6/2014 | Lai et al. |
| 8,877,812 | B2 | 11/2014 | Lai et al. |
| 9,227,777 | B2 * | 1/2016 | Steven .................. A23L 33/40 |
| 9,668,942 | B2 | 6/2017 | Margolin et al. |
| 2005/0129830 | A1 | 6/2005 | Kolke et al. |
| 2006/0121017 | A1 | 6/2006 | Margolin et al. |
| 2007/0007201 | A1 | 1/2007 | Lupton |
| 2007/0269355 | A1 | 11/2007 | Malmqvist |
| 2009/0123634 | A1 | 5/2009 | Klemann et al. |
| 2010/0075900 | A1 | 3/2010 | Zwijsen et al. |
| 2010/0239559 | A1 | 9/2010 | Freedman et al. |
| 2010/0304357 | A1 | 12/2010 | Meyers |
| 2011/0150944 | A1 | 6/2011 | Rozen et al. |
| 2012/0172434 | A1 | 7/2012 | Lai |
| 2012/0279939 | A1 | 11/2012 | Lee |
| 2014/0249224 | A1 | 9/2014 | Lai et al. |
| 2015/0140161 | A1 | 5/2015 | Lai et al. |
| 2015/0246102 | A1 | 9/2015 | Margolin et al. |
| 2016/0017272 | A1 | 1/2016 | Gjerde |
| 2017/0105903 | A1 | 4/2017 | Gallotto et al. |

FOREIGN PATENT DOCUMENTS

| | | | |
|---|---|---|---|
| DE | 2935546 A1 | 3/1981 | |
| JP | 54-132291 A | 10/1979 | |
| JP | 60-027380 A | 2/1985 | |
| JP | 01-231848 A | 9/1989 | |
| JP | 01-273579 A | 11/1989 | |
| JP | 11-502450 A | 3/1999 | |
| JP | 2004-248671 A | 9/2004 | |
| JP | 2005-272307 A | 10/2005 | |
| JP | 2007-524674 A | 8/2007 | |
| JP | 2007-526943 A | 9/2007 | |
| JP | 2008-516965 A | 5/2008 | |
| JP | 2009-544780 A | 12/2009 | |
| WO | WO 96/21480 | 7/1996 | |
| WO | WO 97/23190 A1 | 7/1997 | |
| WO | WO 2004/052115 A1 | 6/2004 | |
| WO | WO 2005/072306 A2 | 8/2005 | |
| WO | WO 2005/084129 A | 9/2005 | |
| WO | WO 2006/044529 A1 | 4/2006 | |
| WO | WO 2006/092622 A1 | 9/2006 | |
| WO | WO 2008/054192 A1 | 5/2008 | |
| WO | WO 2008/054208 A2 | 5/2008 | |
| WO | WO 2011/092299 A1 | 8/2011 | |
| WO | WO 2012/019186 A1 | 2/2012 | |
| WO | WO-2013123139 A1 * | 8/2013 | .............. A61P 25/28 |
| WO | WO 2015/020943 A2 | 2/2015 | |
| WO | WO 2016/120318 A1 | 8/2016 | |

OTHER PUBLICATIONS

Anderson and Ma (2009) "Are all n-3 polyunsaturated fatty acids created equal?" *Lipids Health Dis.* 8:33, doi: 10. 1186/1476-511X-8-33 [online], published Aug. 10, 2009 (20 pages).

Arterburn et al. (2006) "Distribution, interconversion, and dose response of n-3 fatty acids in humans" *Am. J. Clin. Nutr.*, 83(Suppl.): 1467S-76S.
Bengmark and Jeppsson (1995) "Gastrointestinal surface protection and mucosa reconditioning" *JPEN J. Parenter Enterel Nutr.*, 19(5): 410-5.
Balanza-Martinez et al. (2011) "Therapeutic use of omega-3 fatty acids in bipolar disorder" *Expert Rev. Neurother.*, 11(7); 1029-47.
Bansi et al. (2000) "Fibrosing colonopathy in an adult owing to over use of pancreatic enzyme supplements" *Gut*, 46(2): 283-85.
Basri et al. (1994) "Immobilization of hydrophobic lipase derivatives on to organic polymer beads" *J. Chem. Tech. Biotechnol.*, 59(1):37-44.
Bhushan et al. (2008) "immobilization of Lipase of Entrapment in Ca-alginate Beads" *J. Bioactive Compatible Polymers*, 23(6):552-62.
Birch et al. (2010) "The DIAMOND (DHA Intake and Measurement of Neural Development) Study: A double-masked, randomized controlled clinical trial of the maturation of infant visual acuity as a function of the dietary level of docosahexaenoic acid" *Am. J. Clin. Nutr.* 91 (4): 848-59.
Birch et al. (2010) "The impact of early nutrition on incidence of allergic manifestations and common respiratory illnesses in children" *J. Pediatr.*, 156(6): 902-6.
Bolsover et al. *Cell Biology: A Short Course*, 3rd Ed., John Wiley & Sons, Inc., 2011; p. 39.
Borowitz et al. (1995) "Use of pancreatic enzyme supplements for patients with cystic fibrosis in the context of fibrosing colonopathy" *J. Pediatr.*, 127(5):681-84.
Brenna et al. (2009) "α-Linolenic acid supplementation and conversion to n-3 long-chain polyunsaturated fatty acids in humans" *Prostaglandins Leukot. Essent. Fatty Acids*, 80(2-3):85-91.
Burgess et al. (2000) "Long-chain polyunsaturated fatty acids in children with attention-deficit hyperactivity disorder" *Am. J. Clin. Nutr.*, 71(suppl.): 327S-30S.
Calder (2009) "Fatty acids and immune function: relevance to inflammatory bowel diseases" *Int. Rev. Immunol.*, 28A(6): 506-34.
Chiou et al. (2007) "Immobilization of Lipase to Chiltosan Beads using a Natural Cross-Linker" *Prep. Biochem. Biotechnol.*, 37(3):265-75.
Chung et al. (2008) "Fish oil supplementation of control and (n-3) fatty acid-deficient male rats enhances reference and working memory performance and increases brain regional docosahexaenoic acid levels" *J. Nutr.* 138(6):1165-71.
Clandinin et al. (1994) "Relationship between fatty acid accretion, membrane composition, and biologic functions" *J. Pediatr.*, 125:S25-32.
Damerla et al. (2008) "Pancreatic Enzyme Supplementation in Pancreatic Cancer" *J. Support. Oncol.*, 6:393-6.
Davidson et al. (2004) "Weight Stabilization is Associated with Improved Survival Duration and Quality of Life in Unrespectable Pancreatic Cancer" *Clinical Nutrition*, 23:239-47.
Emi et al. (1994) "Lipoprotein lipase immobilization onto copoly(ethylene/acrylic acid) fiber", *Eur. Polymer J.*, 30(5):589-95.
Elnashar "The Art of Immobilization using Biopolymers, Biomaterials and Nanobiotechnology" Chapter 1 in *Biotechnology of Biopolymers.* Prof. Magdy Elnashar (Ed.), InTech, 2011: pp. 3-32.
Empey et al. (1991) "Fish oil-enriched diet is mucosal protective against acetic acid-induced colitis in rats" *Canadian J. Physiol. Pharma.*, 69(4):480-7.
European Patent Application No. 13749880.4, by Alcresta, Inc.: Extended European Search Report and Opinion, dated Aug. 25, 2015 (9 pages).
Fadiloğlu, Sibel et al., "Olive Oil Hydrolysis by Celite-Immobilized Candida rugosa Lipase," *J. Agric. Food Chem.*, 1998, vol. 46 (9), pp. 3411-3414, Department of Food Engineering, Faculty of Engineering, Gaziantep University, Gaziantep, Turkey.
Fan et al. (2004) "Dietary docosahexaenoic acid suppresses T cell protein kinase C theta lipid raft recruitment and IL-2 production" *J. Immuno/*, 173:6151-60.
Fernàndez-Lorente et al. (2010) "Hydrolysis of Fish Oil by Lipases Immobilized Inside Porous Supports" *J. Am. Oil Chem. Soc.*, doi:10.1007/s11746-10-1728-1 [online], published Dec. 14, 2010 (8 pages).

(56) References Cited

OTHER PUBLICATIONS

Fernàndez-Lorente et al. (2011) "rELEASE of Omega-3 Fatty Acids by the Hydrolysis of Fish Oil Catalyzed by Lipases Immobilized on Hydrophobic Supports" *J. Am. Oil Chem. Soc.*, 88:1173-78.
Forsyth et al. (1999) "A randomized controlled study of the effect of long chain polyunsaturated fatty acid supplementation on stool hardness during formula feeding" *Arch. Dis. Child*, 81:253-6.
Gadek et al. (1999) "Effect of enteral feeding with eicosapentaenoic acid, gamma-linolenic acid, and antioxidants in patients with acute respiratory distress syndrome" *Grit. Care Med.*, 27(8):1409-20.
Graham (1977) "Enzyme replacement therapy of exocrine pancreatic insufficiency in man. Relations between in vitro enzyme activities and in vivo potency in commercial pancreatic extracts" *N. Engl. J. Med.*, 296(23):1314-17.
Greenberger et al. (1966) "Absorption of Medium and Long Chain Triglycerides: Factors Influencing Their Hydrolysis and Transport" *J. Clin. Invest.*, 45(2):217-27.
Gunnlaugsdottir et al. (1998), "Alcoholysis and Glyceride Synthesis with Immobilized Lipase on Controlled-Pore Glass of Varying Hydrophobicity in Supercritical Carbon Dioxide," *Enzyme and Microbial. Tech.*, 22:360-367.
Gustafsson, H. (2012) "Enzyme Immobilization in Mesoporous Silica" Thesis for the Degree of Licentiate of Engineering, Department of Chemical and Biological Engineering, Chalmers University of Technology; Göteborg, Sweden.
Herzig et al. (2011) "Fecal pancreatic elastase-1 levels in older individuals without known gastrointestinal diseases or diabetes mellitus" *BMC Geriatrics*, 11-4, dol:10.1186/1471-2318-11-4 [online], published Jan. 25, 2011 (5 pages).
Horrocks et al. (1999) "Health benefits of docosahexaenoic acid (DHA)" *Pharmacological Res.* 40(3):211-25.
Hudert et al. (2006) "Transgenic mice rich in endogenous omega-3 fatty acids are protected from colitis" PNAS, 103(30): 11276-11281.
Innis (2003) "Perinatal biochemistry and physiology of long-chain polyunsaturated fatty acids" *J. Pediatr.*, 143:S1-S8.
International Search Report and Written Opinion dated May 9, 2013, in International Patent Application No. PCT/US2013/026063 (Alcresta, Inc.) (10 pages).
International Search Report and Written Opinion dated Feb. 8, 2017, in international Application No. PCT/US2016/056722 (11 pages).
ISSFAL (International Society for the Study of Fatty Acids and Lipids) (Jul. 2, 2014) "Omega-3 Fats May Reduce Risk of Gastrointestinal Diseases" Press Release [online]. Retrieved from: http://www.issfal.org/news/articles/2014/07102/omega-3-fats-may-reduce-risk-of-gastrointestinal-diseases (2 pages).
Jensen et al. (1983) "Determination of lipase specificity" *Lipids*, 18(3):239-52.
Jensen et al. (1985) "Specificity of Human Milk Bile Salt-Stimulated Lipase" *J. Pediatr. Gastroentrol. Nutr.*, 4:580-2.
Jensen et al. (1986) "Absorption of individual fatty acids from long chain or medium chain triglycerides in very small infants" *Am. J. Clin. Nutr.*, 43:745-51.
Jicha and Markesbery (2010) "Omega-3 fatty acids: potential role in the management of early Alzheimer's disease" *Clin. Interv. Aging*, 5:45-61.
Kalivianakis et al. (1999) "Fat malabsorption in cystic fibrosis patients receiving enzyme replacement therapy is due to impaired intestinal uptake of long-chain fatty acids" *Am. J. Clin. Nutr.*, 69:127-34.
Koletzo et al. (2008) "The roles of long-chain polyunsaturated fatty acids in pregnancy, lactation and infancy: review of current knowledge and consensus recommendations" *J. Perinat. Med.*, 36(1):5-14.
Kris-Etherton et al. (2002) "Fish consumption, fish oil, omega-3 fatty acids, and cardiovascular disease" *Circulation*, 106:2747-57.
Lapillone et al. (2009) "Reevaluation of the DHA requirement for the premature infant" *Prostaglandins, Leukotrines and Essential Fatty Acids*, 81:143-50.

Last "Lipase and the Fat Metabolism" LIPASE—*The Universal Remedy* [online], http://www.health-science-spirit.com/lipase/html, accessed Jul. 24, 2012 (8 pages).
Lauritzsen et al. (2001) "The essentiality of long chain n-3 fatty acids in relation to development and function of the brain and retina" *Prog. Lipid Res.*, 40:1-94.
Lie et al. (1991) "Hydrolysis and esterification with immobilized lipase on hydrophobic and hydrophilic zeolites" *J. Chem. Tech. Biotechnol*, 50:549-53.
Logan et al. (2004) "Omega-3 fatty acids and major depression: A primer for the mental health professional" *Lipids Health Dis.*, 3:25, doi:10.1186/1476-511X-3-25 [online]; published Nov. 9, 2004 (8 pages).
Malone (2005) "Enteral Formula Selection: A Review of Selected Product Categories" *Pract. Gastr.*, 26(6:44-74) (19 pages).
Mañé et al. (2009) "Partial Replacement of Dietary (n-6) Fatty Acids with Medium-Chain Triglycerides Decreases the Incidence of Spontaneous Colitis in Interleukin-10-Deficient Mice" *J. Nutr.*, 139:603-10.
Martek Press Release (May 4, 2010), "Study Published in Alzheimer's & Dementia: The Journal of the Alzheimer's Association Shows Algal DHA Improved Memory and Learning in Healthy Adults Age 55 and older" [online]. Downloaded from http://www.prweb.com/releases/MIDAS/DHA/prweb.com/releases/MIDAS/DHA/prweb3955084.htm on Jan. 9 2015 (2 pages).
Martin et al. (2011) "Decreased Postnatal Docosahexaenoic and Arachidonic Acid Blood Levels in Premature Infants are Associated with Neonatal Morbidities" *J. Pediatr.*, 159(5): 743-49.
Martinez et al. (1992) "Tissue levels of Polyunsaturated Fatty Acids During Early Human Development" *J. Pediatr.*, 120:S129-S138.
McCann et al. (2005) "Is docosahexaenoic acid, an n-3 long-chain polyunsaturated fatty acid, required for development of normal brain function? An overview of evidence from cognitive and behavioral tests in humans and animals" *Am. J. Clin. Nutr.*, 82:281-95.
McDaniel et al. (2011) "Fish oil supplementation alters levels of lipid mediators of inflammation in microenvironment of acute human wounds" *Wound Repair Regen.*, 19(2):189-200.
McNamara et al. (2008) "Deficits in docosahexaenoic acid and associated elevations in the metabolism of arachidonic acid and saturated fatty acids in the postmortem orbitofrontal cortex of patients with bipolar disorder" *Psychiatry Res.*, 160(3):285-99.
McNamara et al. (2010) "Docosahexaenoic acid supplementation increases prefrontal cortex activation during sustained attention in healthy boys: a placebo-controlled, dose-ranging, functional magnetic resonance imaging study" *Am. J. Nutr.*, 91:1060-67.
McNamara et al. (2010) "Selective deficits in erythrocyte docosahexaenoic acid composition in adult patients with bipolar disorder and major depressive disorder" *J. Affect. Disord.*, 126(1-2):303-11.
Milligan and Bazinet (2008) "Evolutionary modifications of human milk composition: evidence from long-chain polyunsaturated fatty acid composition of anthropoid milks" *J. Human Evol.*, 55:1086-95.
Mu (2008) "Bioavailability of omega-3 long-chain polyunsaturated fatty acids from foods" *AgroFOOD Industry Hi Tech Supplement*, 19(4):24-6.
Murty et al. (2002) "Hydrolysis of Oils Using Immobilized Lipase Enzyme: A Review" *Biotechnol. Bioprocess Eng.*, 7:57-66.
Nestlé (2011) "Gerber® Infant Formulas Nutrient Comparison Chart" (8 pages).
Nieto et al. (1999) "Synthesis of structured triacylglycerols containing medium-chain and long-chain fatty acids by interesterfication with a stereospecific lipase from *Mucor miehel*" *Grasas y Aceites*, 50(3):199-202.
Oh et al. (2010) "GPR120 is an omega-3 fatty acid receptor mediating potent anti-inflammatory and insulin-sensitizing effects" *Cell*, 142(5):687-98.
Oksman et al. (2006) "Impact of different saturated fatty acid, polyunsaturated fatty acid and cholesterol containing diets on beta-amyloid accumulation in APP/PS1 transgenic mice" *Neurobiol. Dis.*, 23(3):563-72.

(56) References Cited

OTHER PUBLICATIONS

Peretti et al. (2005) "Mechanisms of lipid malabsorption in Cystic Fibrosis: the impact of essential fatty acids deficiency" *Nutrition & Metabolism*, 2:11, doi: 10.1186/1743-7075-2-11 [online]; published May 3, 2005 (18 pages).

Pérez et al. (2011) "A Novel Halophilic Lipase, LipBL, Showing High Efficiency in the Production of Eicosapentaenoic Acid (EPA)" *PLoS ONE*, 6(8):e23325, doi:10.1371/journal.pone.0023325 [online], published Aug. 10, 2011 (11 pages).

Pointes-Arruda et al. (2006) "Effects of enteral feeding with eicosapentaenoic acid, y-linolenic acid, and antioxidants in mechanically ventilated patients with severe sepsis and septic shock" *Crit. Care Med.*, 34(9):2325-33.

Reisbick et al., (1997) "Visual Attention in infant monkeys: effects of dietary fatty acids and age" *Dev. Psychol.*, 33(3):387-95.

Ren et al. (2011) "Facile, high efficiency immobilization of lipase enzyme on magnetic iron oxide nanoparticles via a biomimetic coating" *BMC Biotechnol.*, 11:63, dol: 10.1186/1472-6750-11-63 [online], published Jun. 8, 2011 (8 pages).

Ruthig and Meckling-Gill (1999) "Both (n-3) and (n-6) fatty acids stimulate wound healing in the rat intestinal epithelial cell line, IEC-6" *J. Nutr.* 129:1791-98.

Sanderson et al. (1997) "Dietary fish oil diminishes the antigen presentation activity of rat dendritic cells" *J. Leukoc. Biol.*, 62:771-7.

Sangiovanni and Chew (2005) "The role of omega-3 long chain polyunsaturated fatty acids in health and disease of the retina" *Progr. Retinal Eye Res.*, 24:87-138.

Sarkadi-Nagy et al. (2004) "Formula feeding potentiates docosahexaenoic and arachidonic acid biosynthesis in term and preterm baboon neonates" *J. Lipid Res.*, 45:71-80.

Scheltens et al. (2012) "Efficacy of Souvenaid in Mild Alheimer's Disease: Results from a Randomized Controlled Trial" *J. Alzheimer's Dis.*, 31:225-36.

Stark and Holmberg (1989) "Covalent immobilization of lipase in organic solvents" *Biotechnol. Bioeng.*, 34(7):942-50.

Stoll et al. (1999) "Omega 3 Fatty Acids in Bipolar Disorder. A Preliminary Double-blind, Placebo-Controlled Trial" *Arch. Gen Psychiatry*, 56(5):407-12.

Toyo Denka Kogyo Co., Ltd. (Date unknown) "New Inorganic Carriers for Immobilization of Enzymes. *Toyonite*" (12 pages).

Ville et al. (2002) "Physiological study of pH stability and sensitivity to pepsin of human gastric lipase" *Digestion*, 65:73-81.

Yuhas et al. (2006) "Human milk fatty acid composition from nine countries varies most in DHA" *Lipids*, 41(9):851-58.

* cited by examiner

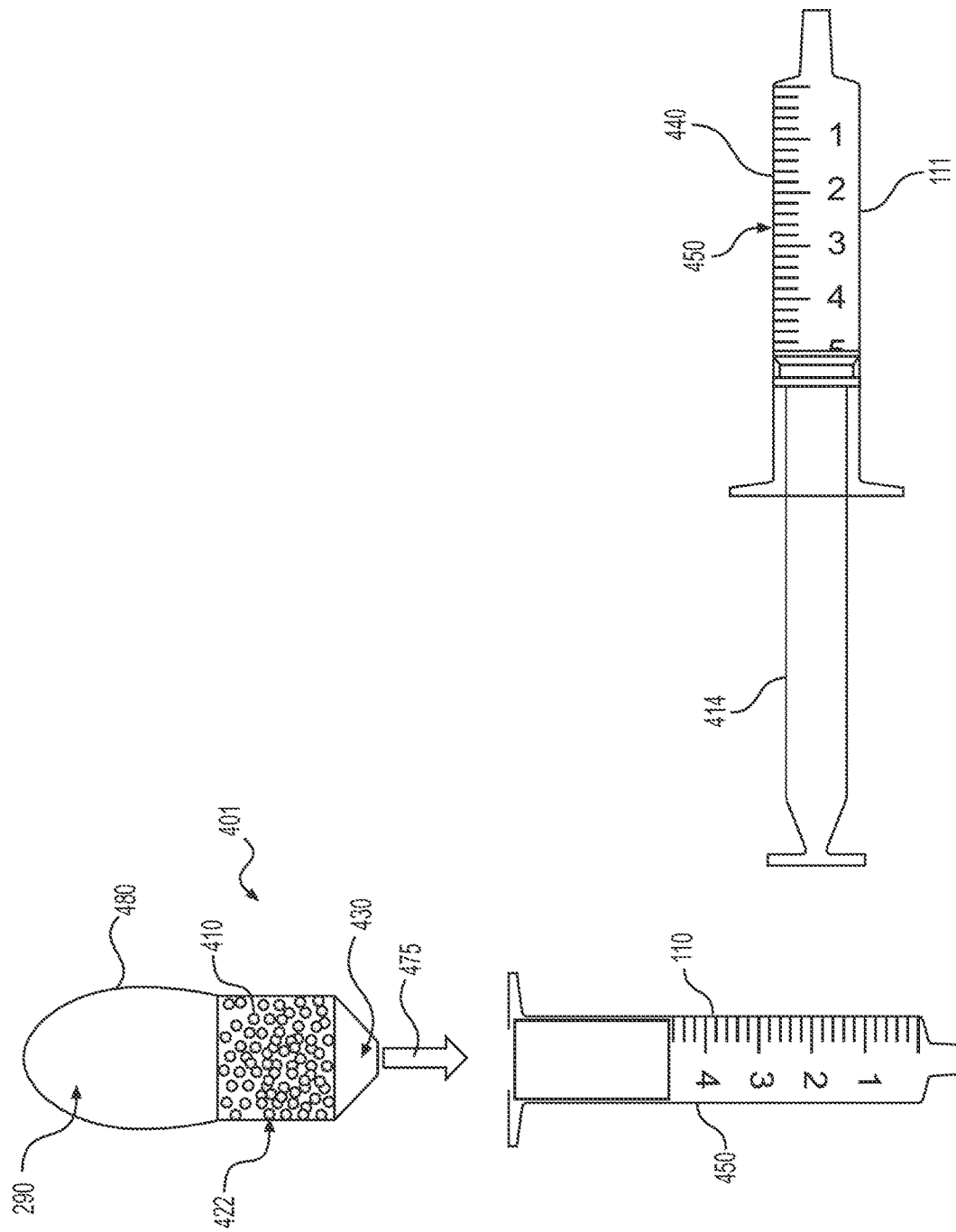

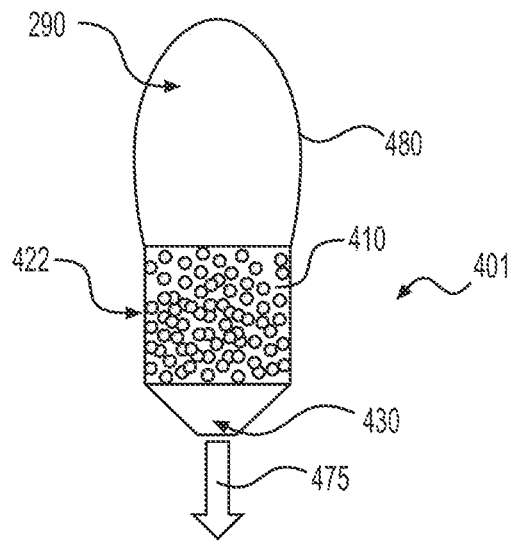
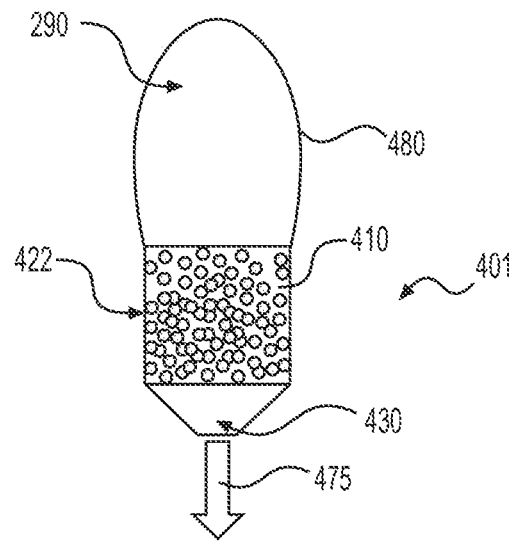
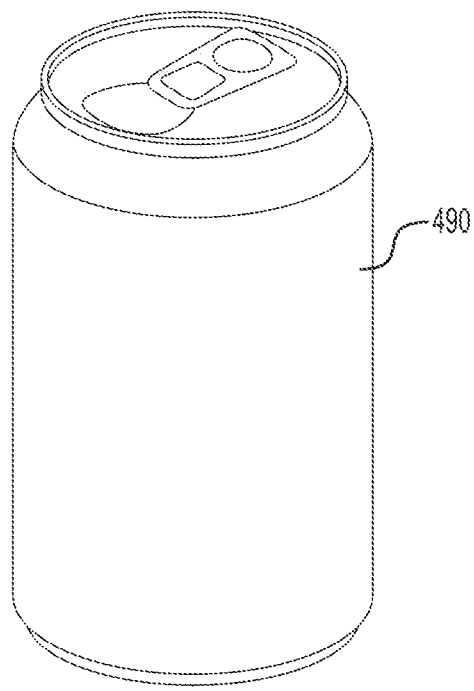
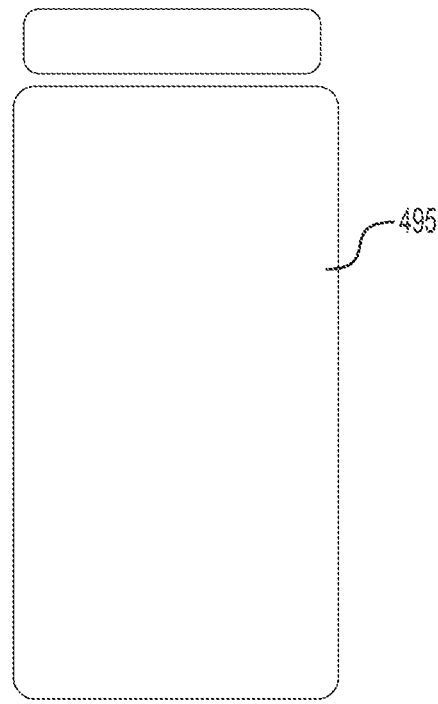
FIG. 10A     FIG. 10B

DEVICES AND METHODS FOR THE SUPPLEMENTATION OF A NUTRITIONAL FORMULA

CROSS-REFERENCE TO RELATED APPLICATIONS

This application claims the benefit of priority from U.S. Provisional Application No. 62/546,817, filed on Aug. 17, 2017, the entirety of which is incorporated herein by reference.

FIELD OF THE DISCLOSURE

Embodiments of the present disclosure are directed to devices and methods for preparing and/or supplementing a nutritional formula, and more particularly, to devices and methods for supplementing a nutritional formula with hydrolyzed lipids from a lipid source.

BACKGROUND

Premature infants are often born with an immature gastrointestinal (GI) system. As a result, premature infants may require specific forms of nutrients for their GI systems to digest, which may be provided in one or more nutritional formulas, so that they receive proper nutrition. Premature infants are often given parenteral nutrition (PN) within hours of birth. Small amounts of nutrition via PN may be administered while beginning to prime an infant's GI system. As infants begin to tolerate larger volumes, they may be weaned off of PN and transitioned to oral or enteral feeds, which generally consist of one or more nutritional formulas, including, e.g., mother's own milk (MoM), donor mother's milk (DM), infant formula (IF) and/or additional nutritional fortifiers. It may be preferred to use exclusively MoM; however, a mother may not be able to supply enough milk to provide the required daily calories for optimal growth and development. To make up this deficit, MoM may be supplemented, e.g., with DM, which may be collected, screened, and/or heat pasteurized. In some instances, it may be less preferred to use infant formula, but MoM and DM may be inherently low in calories. Additionally, the number of human milk banks is rapidly increasing worldwide, yet they are largely unregulated, and the calorie and nutrient content of the milk they provide may vary considerably.

Long-chain fatty acids are important to human health and development. Many long-chain fatty acids are consumed as triglycerides, in which three long-chain fatty acids are bound to a glycerol molecule via ester linkages. Absorption of long-chain triglycerides (LCTs) by the body first requires the enzymatic action of lipases (e.g., pancreatic lipase) and bile salts, which digest triglycerides through hydrolysis, breaking them down into a monoglyceride and two free fatty acids. Digestion products consisting of a mixture of tri-, di-, and monoglycerides and free fatty acids, which, together with the other fat soluble contents of the diet (e.g., the fat soluble vitamins and cholesterol) and bile salts, form mixed micelles in the watery duodenal contents. Once broken down, the monoglycerides and free fatty acids may be absorbed by enterocytes—epithelial cells lining the small intestine—for example, in the region of the jejunum. The contents of these micelles (but not the bile salts) enter the enterocytes, where they are resynthesized into triglycerides and packaged into chylomicrons, which are released into the lacteals (the capillaries of the lymph system of the intestines). Medium-chain triglycerides (MCTs) are absorbed directly into the bloodstream.

Exocrine pancreatic function may not be fully developed at birth in premature infants, and so premature infants may lack sufficient quantities of the enzyme lipase, which is necessary to break down triglycerides. At birth, the mother provides an "on-board lipase," called bile salt-stimulated lipase (BSSL), also known as carboxyl ester lipase or bile salt-dependent lipase, which is provided to the infant through breast milk. While this may partially compensate for poor endogenous production, BSSL production may be insufficient for supporting proper fat absorption. Additionally, the majority of fats in mother's milk are in the form of palmitic acid (n-16), which is an MCT, and thus mother's milk may lack sufficient LCTs, e.g., those containing docosahexaenoic acid (DHA, 22:6 n-3) and arachidonic acid (ARA 20:4 n-6), which are critical in membrane structure, function, and neuronal, retinal, and other tissue development. In donor milk, during the pasteurization process, lipase that was present may be inactivated by exposure to high heat, and thus LCT fats are not as readily broken down. As a result, an infant may suffer from feeding intolerance due to the inability to absorb these larger LCTs, irritating the gut mucosa and initiating localized inflammation.

Human milk may not meet the high daily nutrient requirements of a very low body weight infant. For example, standard fortification of human milk designed to optimize nutritional intake often falls short of the nutrient requirements with regard to protein and fats. This problem may be further amplified with the use of donor milk, which is often donated by the mothers of term infants beyond 1 month postpartum, and which is likely to have lower protein and fat content than preterm mothers' milk.

The fat and protein content of human milk is extremely variable, and protein decreases with lactation duration. In recent years, it has become evident that preterm infants fed fortified human milk (mother's milk or donor milk) receive less protein than assumed and continue to grow more slowly in the short term, even with standard human milk fortification. Although there is some uncertainty about optimal growth, postnatal growth failure has not been solved with human milk fortification in standard fashion. Thus, there is a need for improved fortification of human milk to achieve better short-term infant growth, which is associated with improved neurocognitive outcomes, among other improvements. The ability to more efficiently process and absorb LCTs may lead to better overall nutrient absorption and thus growth.

For at least the above reasons, current infant nutritional formula (including mother's milk, donor milk, infant formula, and/or fortifiers) may lack sufficient nutrient density for premature infants. Accordingly, methods and devices to increase nutrient density in nutritional formula for premature infants are needed. Further, patients suffering from various malabsorption impairments may be unable to adequately digest LCTs and other forms of fat through hydrolysis, inhibiting absorption of the fatty acids required to maintain health. Exemplary impairments include, but are not limited to, the following: compromised pancreatic output, acute and chronic pancreatitis, pancreatic cancer, pancreatic insufficiency, cystic fibrosis, cerebral palsy, Crohn's disease, irritable bowel syndrome, chronically abnormal epithelium, amyloidosis, celiac disease, Crohn's disease, ischemia, radiation enteritis, tropical sprue, Whipple disease, inadequate gastric mixing, rapid emptying, or both, Billroth II gastrectomy, gastrocolic fistula, gastroenterostomy, insufficient digestive agents, biliary obstruction and cholestasis, cirrhosis, chronic pancreatitis, cholestyramine-induced bile acid loss, cystic fibrosis, lactase deficiency, pancreatic cancer, pancreatic resection, sucrase-isomaltase deficiency, abnormal milieu, abnormal motility secondary to diabetes, scleroderma, hypothyroidism, or hyperthyroidism, bacterial overgrowth due to blind loops (deconjugation of bile salts), diverticula in the small intestine, Zollinger-Ellison syndrome (low duodenal pH), acutely abnormal epithelium, acute intestinal infections, alcohol, neomycin, impaired transport, abetalipoproteinemia, Addison disease, blocked lacteals due to lymphoma or tuberculosis, intrinsic factor deficiency (as in pernicious anemia), lymphangiectasia, jejunoileal bypass for obesity, short bowel syndrome, or other conditions. Other patients may need or want additional dietary supplementation. Further improvements are required to address these and other known issues.

SUMMARY

Exemplary embodiments of the disclosure may be drawn to a device having a vessel configured to contain a source of lipids and a chamber fluidly connected to an outlet of the vessel. The chamber may contain immobilized lipase positioned within a flow path in the chamber along which the lipids flow when released from the vessel into the chamber. The device may also include an outlet through which the lipids flow after passing through the chamber.

Various embodiments of the device may include one or more of the following features. The vessel may be sealed except for the outlet, the vessel may be removably coupled to the chamber, or the vessel may be compressible. The device may also include a connector fluidly coupled to the outlet, and the connector may include a first opening for receiving a flow of fluid, a second opening for outputting the flow of fluid, and a connector flow path extending through the connector from the first opening to the second opening, wherein the connector flow path is fluidly connected to the output assembly. The device may also have an interface located between the connector and the outlet through which the lipids flow from the outlet and into the connector, and the interface may be removably connected to the connector. In some aspects, the device may include a source of lipids contained within the vessel, and the lipids may include two or more different types of lipids.

In other exemplary embodiments, a device may include a vessel, a source of lipids contained within the vessel, a chamber coupled to an opening in the vessel, and an output assembly coupled to the chamber. A flow path may extend from the opening in the vessel, through the chamber, and through the output assembly along which the lipids flow through the device when released from the vessel. The device may also include immobilized lipase contained within the chamber and located within the flow path, wherein the lipase is configured to hydrolyze the lipids as the lipids flow through the chamber.

Various embodiments of the device may include one or more of the following features. The vessel may include only one opening, the vessel may be compressible, and the output assembly may have a first end and a second end, wherein the first end is coupled to the chamber, and the first end has a width that is greater than a width of the second end. In some aspects, the output assembly may have a first end and a second end, wherein the first end is coupled to the chamber, and the second end has an opening that is covered by a seal when the lipids are contained within the vessel and is uncovered by the seal when the lipids are flowing along the flow path. In some embodiments, the lipids may include two or more different types of lipids.

In other exemplary embodiments, a method of supplementing a nutritional formula with hydrolyzed lipids may include passing a source of lipids stored in a device through a chamber of the device that contains immobilized lipase in order to hydrolyze the lipids by exposing the lipids to the lipase in the chamber. The method may also include outputting the hydrolyzed lipids from the chamber of the device, and adding the hydrolyzed lipids to the nutritional formula.

Various embodiments of the method may include one or more of the following features. The nutritional formula may be flowed past the device as the hydrolyzed lipids are added to the nutritional formula, the method may further include preparing the source of lipids prior to passing the lipids through the chamber, and preparing the source of lipids may include mixing at least two different types of lipids together. In some aspects, the source of lipids may be stored in a vessel of the device prior to being passed through the chamber, and the method may further include attaching the vessel to the device prior to passing the source of lipids through the chamber. The method may also include attaching the device to a feeding system prior to passing the source of lipids through the chamber, and the method may also include feeding the nutritional formula to a patient after the hydrolyzed lipids have been added to the nutritional formula. In some aspects, adding the hydrolyzed lipids to the nutritional formula may include outputting the hydrolyzed lipids from the device and into a container containing the nutritional formula.

Both the foregoing general description and the following detailed description are exemplary and explanatory only and are not restrictive of the features, as claimed. As used herein, the terms "comprises," "comprising," "includes," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." It should be noted that all numeric values disclosed or claimed herein (including all disclosed values, limits, and ranges) may have a variation of +/−10% (unless a different variation is specified) from the disclosed numeric value. Moreover, in the claims, values, limits, and/or ranges means the value, limit, and/or range +/−10%.

BRIEF DESCRIPTION OF THE DRAWINGS

The accompanying drawings, which are incorporated in and constitute a part of this specification, illustrate the disclosed embodiments, and together with the description, serve to explain the principles of the disclosed embodiments. There are many aspects and embodiments described herein. Those of ordinary skill in the art will readily recognize that the features of a particular aspect or embodiment may be used in conjunction with the features of any or all of the other aspects or embodiments described in this disclosure. In the drawings:

FIGS. 9A and 9B illustrate an exemplary device being used with an exemplary feeding system, according to embodiments of the present disclosure.

FIG. 10A illustrates a feeding system for use with an exemplary device for supplementing a nutritional formula, according to embodiments of the present disclosure.

FIG. 10B illustrates a feeding system for use with an exemplary device for supplementing a nutritional formula, according to embodiments of the present disclosure.

DETAILED DESCRIPTION

Figure 1A:
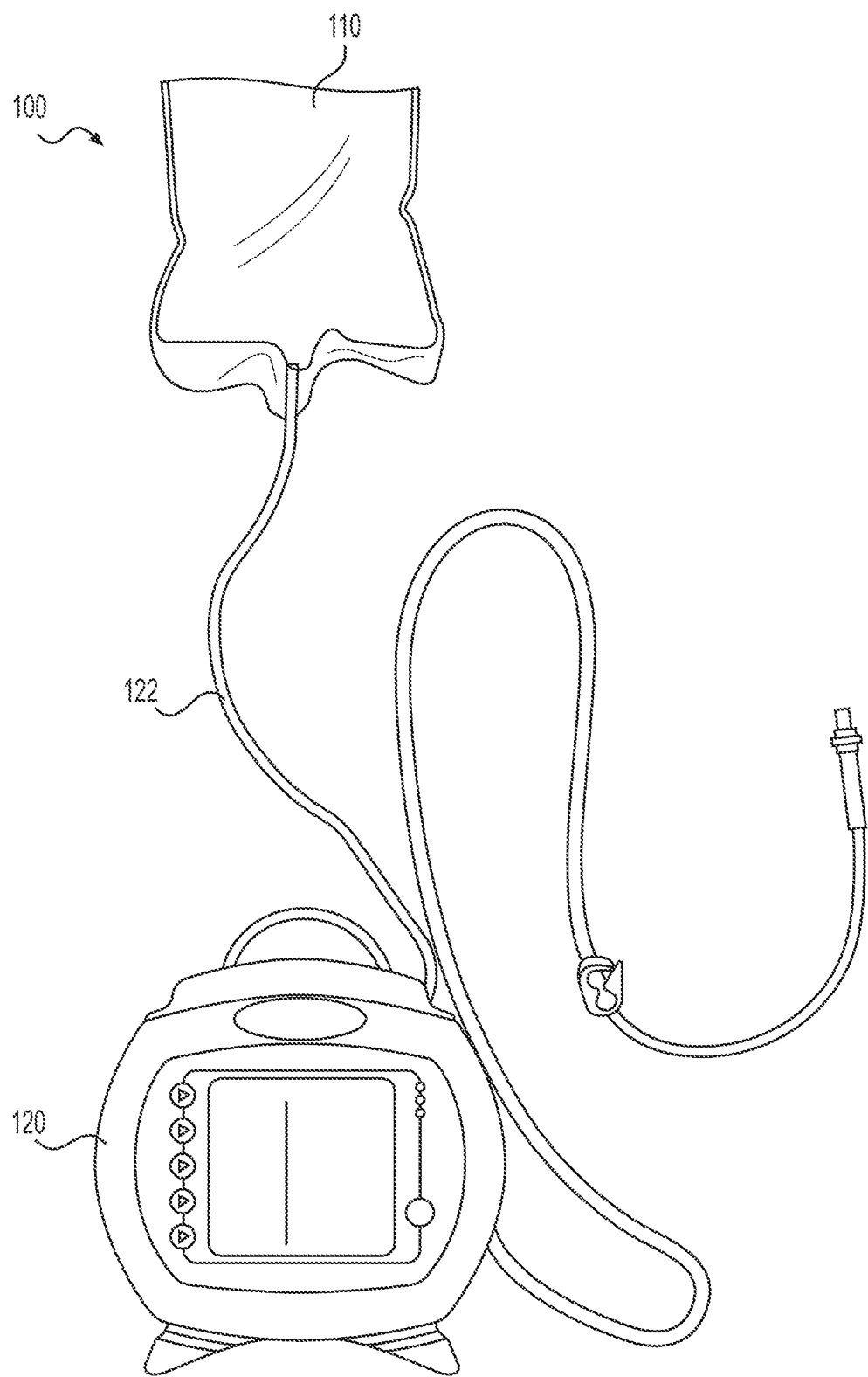
FIG. 1A illustrates an exemplary feeding system, according to embodiments of the present disclosure.

Reference will now be made in detail to the exemplary embodiments of the present disclosure described below and illustrated in the accompanying drawings. Wherever possible, the same reference numbers will be used throughout the drawings to refer to same or like parts.

Additional objects and advantages of the embodiments will be set forth in part in the description that follows, and in part will be obvious from the description, or may be learned by practice of the embodiments. It is to be understood that both the foregoing general description and the following detailed description are exemplary and explanatory only and are not restrictive of the claims.

Aspects of the present disclosure are described with reference to devices for supplementing nutritional formulas, and, particularly, to devices for hydrolyzing lipids. Although embodiments of the disclosure are generally described in reference to human milk (e.g., mother's milk or donor milk, either pasteurized or unpasteurized), it will be understood that embodiments of the disclosure may be used to supplement (e.g., with hydrolyzed lipids) any nutritional formula or beverage.

As used herein, the term "nutritional formula" may include complex mixtures containing, for example, proteins, carbohydrates, fat, water, minerals, and/or vitamins. This may include liquid foods that are specially formulated and processed; liquids used for the partial or exclusive feeding of a person by means of oral intake or feeding by tube; liquids used for the dietary management of a person who, because of therapeutic or medical need, has limited or impaired capacity to ingest, digest, absorb, or metabolize ordinary foodstuffs or certain nutrients; liquids that meet medically determined nutrient requirements; and liquids designed to deliver to a subject nutrients that cannot be provided to the subject via dietary management and modification of the normal diet alone.

In some embodiments, nutritional formula 110 may be delivered to the subject under medical supervision, may be intended only for a person receiving active and ongoing medical supervision, or may be delivered to the subject for home use, either when supervised or unsupervised. Nutritional formula 110 may be packaged as a dry powder and then mixed with a solvent to form a solution or may be packaged as a liquid nutritional formula, beverage, or drink. In some embodiments, nutritional formula 110 may be commercially available, or may be prepared by a healthcare professional before feeding. In some embodiments, nutritional formula 110 may include at least one medicament prescribed for the subject in need of the medicament and/or nutritional formula 110, or nutritional formula 110 may itself be the prescribed medicament. Nutritional formula 110 may be an infant and/or toddler formula as a complete or partial substitute for human milk, may be donor milk, or mother's milk (infant's own mother or other mother's milk), whether pasteurized or unpasteurized.

Nutritional formula 110 may or may not include at least one fat in triglyceride form, such as MCTs and LCTs. In some embodiments, nutritional formula 110 may further include at least one nutrient selected from water, maltodextrin, protein, hydrolyzed protein, amino acids, peptides, MCTs, diglycerides, monoglycerides, cornstarch, fish oil, soybean oil, rapeseed oil, cottonseed oil, sunflower oil, olive oil (oils may or may not be refined), soluble fiber, lecithin, magnesium chloride, sodium ascorbate, guar gum, calcium phosphate, salt, choline chloride, phosphoric acid, calcium citrate, sodium phosphate, taurine, magnesium oxide, zinc sulfate, potassium chloride, niacinamide, ferrous sulfate, calcium pantothenate, manganese sulfate, pyridoxine hydrochloride, copper sulfate, thiamine mononitrate, beta-carotene, riboflavin, vitamin a palmitate, folic acid, biotin, sodium selenate, chromium chloride, potassium iodide, sodium molybdate, soluble fiber, fructooligosaccharide, probiotic, citric acid, vitamin A, vitamin D, vitamin E, vitamin $B_1$, vitamin $B_2$, vitamin $B_3$, vitamin $B_5$, vitamin $B_6$, vitamin $B_7$, vitamin $B_6$, and vitamin $B_{12}$. Exemplary nutritional formulas and systems are described in U.S. patent application Ser. No. 14/378,856, filed Aug. 14, 2014, now U.S. Pat. No. 9,668,942, which is herein incorporated by reference in its entirety.

As described above, in some aspects, exemplary nutritional formulas may not contain sufficient amounts of nutrients, e.g., lipids, for the needs of a patient, e.g., a premature infant, or a patient may want further supplementation. Embodiments of the present disclosure may be used to provide a nutritional formula that, as-fed, delivers increased concentrations of hydrolyzed lipids, e.g., of monoglycerides and free fatty acids, which may be absorbed through the gut of an infant or other patient. As a result, formula-fed subjects may be provided with, e.g., one or more of docosahexaenoic acid ("DHA"), eicosapentaenoic acid ("EPA"), arachidonic acid ("ARA" or "AA"), or other lipids that they may not otherwise have had access to or may not have been able to digest. Some embodiments may be used to supplement mother's milk, donor breast milk, and/or infant formulas using a lipid source, such as supplemental oils and/or infant fortifiers. Some embodiments of the disclosure may provide a method to hydrolyze one or more triglyceride molecules from a lipid source to produce free fatty acids and monoglycerides for addition to a nutritional formula, such as mother's breast milk, donor breast milk, or infant formulas.

Embodiments of the present disclosure are drawn to devices and methods for increasing the amount of total calories and/or energy in nutritional formulas while not significantly increasing the overall volume of nutritional formula fed to the patient (e.g., by increasing the nutrient density of the formula). By not substantially increasing the amount of formula to be fed to a patient, or by decreasing the volume of nutritional formula to be fed to a patient due to the increased concentration of nutrients, embodiments of the present disclosure may reduce inflammatory responses found in the patient's (e.g., a premature infant's) GI tract and/or may condition the patient's GI tract for improved overall absorption of nutrients, including, but not limited to, protein and vitamins.

Exemplary devices may include a vessel for containing a lipid source and a chamber containing immobilized lipase through which the lipid source may be passed in order to hydrolyze the lipids. Exemplary devices may be fluidly connected to a source of nutritional formula and/or a feeding system for delivering a nutritional formula in order to supplement the nutritional formula with the hydrolyzed lipids. Exemplary devices and exemplary systems in which they may be included are described further below.

FIG. 1A illustrates an exemplary feeding system 100 for providing a nutritional formula 110 to a subject, e.g., via a feeding tube. In some embodiments, system 100 may be an enteral feeding system. As shown in later figures, devices of the present disclosure may be incorporated in numerous different ways into system 100 to supplement nutritional formula 110 with hydrolyzed lipids.

An exemplary system 100 may include a pump 120 and a tube 122 fluidly connecting a source of nutritional formula 110 to an outlet configured to output nutritional formula 110 to a patient for ingestion. Nutritional formula 110 may be contained in, e.g., a feeding bag, a vial, a syringe, a bottle, or any other suitable container. Nutritional formula 110 may be flowed from the source, through tube 122, and to the patient. Tube 122 may be an enteral feeding tube, for example, a gastric, a nasogastric, a nasoduodenal, a nasojejunal, a gastrostomy, a gastrojejunostomy, a jejunostomy, a percutaneous endoscopic gastrostomy (PEG) tube, or a transjejunal feeding tube to feed nutritional formula 110 to the GI tract of a subject through, for example, the nose, mouth, stomach, or abdomen of the patient. System 100 may be used in line with standard enteral feeding practice.

Figure 1B:
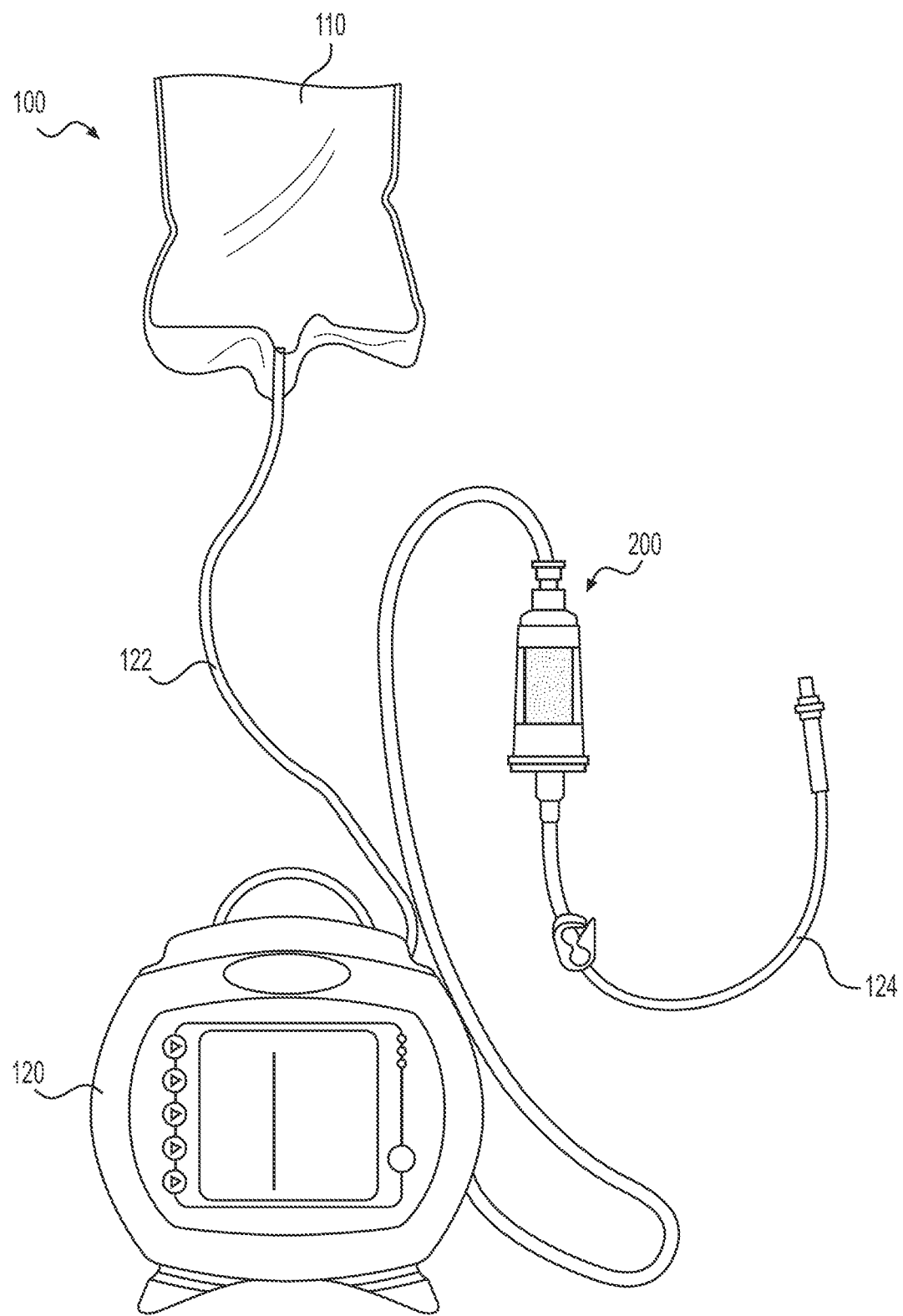
FIG. 1B illustrates an exemplary feeding system, according to embodiments of the present disclosure.

FIG. 1B illustrates another exemplary embodiment of a feeding system 100 for providing a nutritional formula 110 to a subject, e.g., via a feeding tube. System 100 of FIG. 1B may further include a fat hydrolysis device 200, in addition to a pump 120 and a first tube 122 fluidly connecting a source of nutritional formula 110 to device 200. As with the system of FIG. 1A, nutritional formula 110 may be contained in, e.g., a feeding bag, a vial, a syringe, a bottle, or any other suitable container. Nutritional formula 110 may be flowed from the source, through first tube 122, and to device 200, where nutritional formula 110 is hydrolyzed. System 100 also includes a second tube 124 having a first end configured to connect to an outlet of device 200 and a second end, opposite the first end, configured to connect to a patient to deliver processed nutritional formula 110 from device 200 to the patient for ingestion. Second tube 124 may be an enteral feeding tube, for example, a gastric, a nasogastric, a nasoduodenal, a nasojejunal, a gastrostomy, a gastrojejunostomy, a jejunostomy, a percutaneous endoscopic gastrostomy (PEG) tube, or a transjejunal feeding tube to feed nutritional formula 110 to the GI tract of a subject through, for example, the nose, mouth, stomach, or abdomen of the patient. System 100 may be used in line with standard enteral feeding practice. Exemplary embodiments of feeding system 100 and fat hydrolysis device 200 are described in U.S. patent application Ser. No. 15/291,530, filed Oct. 12, 2016, and U.S. patent application Ser. No. 14/378,856, filed Aug. 14, 2014, now U.S. Pat. No. 9,668,942, both of which are herein incorporated by reference in their entireties.

System 100 of FIG. 1B is configured to deliver and process nutritional formula 110 at the point of care to allow device 200 to hydrolyze fats contained in nutritional formula 110 just prior to ingestion. As used herein, "processing" by device 200 may refer to hydrolyzing fats already contained within nutritional formula 110 by exposing nutritional formula 110 to lipases contained within device 200. As shown in later figures, devices of the present disclosure may be incorporated in numerous different ways into system 100 to supplement nutritional formula 110 with additional lipids.

The present disclosure is drawn to devices and methods for supplementing nutritional products in conjunction with systems that may or may not include a fat hydrolysis device 200, or indeed may be used in conjunction with any other feeding system. The systems 100 of FIGS. 1A and 1B are provided only as examples of feeding systems.

At least one benefit of the disclosed devices is that they may allow for the controlled addition of hydrolyzed lipids to a nutritional formula without otherwise impacting the properties of the nutritional formula. Whereas device 200 of FIG. 1B may expose nutritional formula 110 to lipase and may pass nutritional formula 110 through device 200, embodiments of the present disclosure do not pass nutritional formula 110 through them and are structured to allow only a source of lipids through them for hydrolysis, which is then output into nutritional formula 110 to supplement nutritional formula 110. Thus, in some embodiments, only the lipids stored in or otherwise fed into devices of the disclosure may be exposed to lipase, and the resulting hydrolyzed lipids may be added to the formula.

The flow of nutritional formula 110 through systems 100 of FIGS. 1A and 1B may be controlled by pump 120 of system 100. In some embodiments, pump 120 may be a peristaltic pump, although any suitable type of infusion pump, e.g., an elastomeric pump, a multi-channel pump, a syringe pump, and/or a smart pump may be used. A flow rate of nutritional formula 110 through the tubes and/or device 200 may be set and/or adjusted by pump 120. In some embodiments, pump 120 may include a processor, a display, and/or actuators (e.g. buttons, knobs, touch screen, etc.) to adjust and control the flow rate of nutritional formula 110 in system 100 and device 200. Pump 120 may be adjusted and set by a healthcare provider and/or the subject receiving nutritional formula 110. Pump 120 may perform continuous feeding, pulsatile feeding, intermittent feeding, bolus feeding, and/or flushing, and delivery of fluids may be set or adjusted automatically, semi-automatically, or manually.

In other embodiments, systems 100 of FIGS. 1A and 1B may not include pump 120 and may instead depend on gravity to flow nutritional formula 110 from the source to the patient. The relative positioning of the source of nutritional formula 110 may allow nutritional formula 110 to flow through the tubes and, if included, device 200, under the influence of gravity alone. For example, a container of nutritional formula 110 may be placed above the attached tubing, above device 200 (if included), and/or above the patient, as shown in FIGS. 1A and 1B.

In other embodiments, pump 120 of systems 100 may be replaced with a syringe. The syringe may be filled with nutritional formula 110, and the flow rate of nutritional formula 110 in the tubes and/or device 200 (if included) may be set, and/or adjusted by using the syringe manually, semi-automatically, or automatically. For example, nutritional formula 110 may be pre-packaged in a pre-filled syringe mounted inside of an auto-injector-like device. The pre-packaged formula may also contain a pump 'engine' (e.g., a spring-loaded piston), and may be used to deliver the formula through systems 100 and to the patient.

In other embodiments, systems 100 may use any suitable means, e.g., a balloon or other suitable pressure-generating device, to generate a pressure drop or a flow-driving force that drives nutritional formula 110 through the tubes and/or device 200.

The devices and methods disclosed herein may be used to expose a lipid source to lipases to hydrolyze the lipids, which may be subsequently added to nutritional formula 110, which may include, e.g., donor milk, mother's milk, and/or infant formula, prior to consumption. The devices and methods may provide a convenient way to supplement nutritional formula 110 with hydrolyzed lipids, e.g., free fatty acids and monoglycerides. In some embodiments, the devices and methods provide formulas that contain monoglycerides and/or free fatty acids, or an increased concentration of monoglycerides and/or free fatty acids, but do not contain a significant amount of lipase or contain no lipase.

Figure 2:
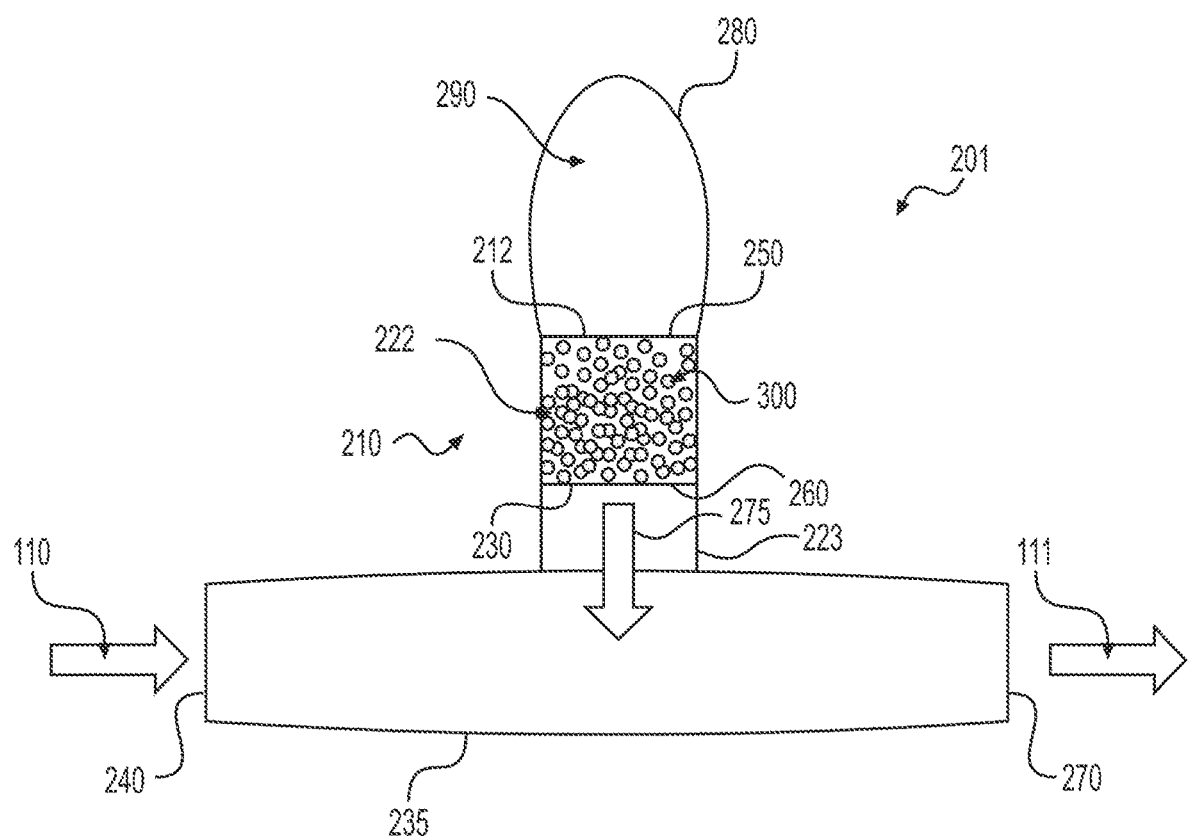
FIG. 2 illustrates an exemplary device for supplementing a nutritional formula, according to embodiments of the present disclosure.

FIG. 2 illustrates an exemplary device 201 in accordance with the present disclosure. Device 201 may include a body 210 having an inlet 212, a chamber 222, and an outlet 230. Chamber 222 may contain a plurality of particles 300 or other structures on which lipase may be immobilized, e.g., via covalent or ionic binding or by absorption, for example. Device 201 may also include an interface 223 through which hydrolyzed lipids 275 may pass out of chamber 222 through outlet 230 and then into a source of nutritional formula 110. In some embodiments, interface 223 may be configured to fluidly connect to a feeding tube or an opening in any other suitable container in which nutritional formula 110 may be stored. In some embodiments, however, outlet 230 of chamber 222 may be configured to directly connect or otherwise output hydrolyzed lipids 275 into nutritional formula 110, and device 201 may not include interface 223.

In the embodiment of FIG. 2, interface 223 is fluidly connected to a connector 235. Connector 235 may be part of device 210 or may be separate from device 210 and configured to removeably connect to device 210 (e.g., via interface 223). Connector 235 may have a first connector end 240 and a second connector end 270. Connector end 240 may be configured to fluidly couple to a source of nutritional formula 110 and to receive an input of nutritional formula 110. Connector end 270 may be configured to fluidly couple to a structure, e.g., a feeding tube, configured to deliver supplemented nutritional formula 111 to a patient and may be configured to discharge an output of supplemented nutritional formula 111 into which interface 223 may have delivered hydrolyzed lipids from chamber 222. For example, in some embodiments, first connector end 240 and second connector end 270 may be configured to fluidly connect to one or both of first tube 122 and enteral tube 124 of system 100 (FIGS. 1A and 1B). As nutritional formula 110 flows through system 100 (or any other system), nutritional formula 110 from a source may be received within connector end 240 and may flow into connector 235. While in connector 235, device 201 may deliver hydrolyzed lipids into nutritional formula 110 to supplement nutritional formula 110, and then supplemented nutritional formula 111 may flow out of connector end 270 for administration to a patient.

Connector end 240 and connector end 270 may include, e.g., a luer-lock connection, threads, projections, grooves, deformable or expandable structures, and/or any other suitable mechanism for connecting to one or more tubes or devices for carrying nutritional formula from a source and/or to a patient. In some embodiments, connector end 240 and connector end 270 may be configured to engage a baby bottle, baby bottle nipple, or any other structure to facilitate transfer of fluid to another container and/or to assist in feeding. Further, one or both of the connector end 240 and connector end 270 may include a valve or other fluid flow control mechanism.

Device 201 may also include a vessel 280 fluidly connected to chamber 222. Vessel 280 may contain a lipid source 290. A flow path may extend from vessel 280, through chamber 222, through outlet 230, and through interface 223 (if included). Lipid source 290 may include one or more lipids, e.g., structured lipids or naturally occurring lipids. Lipid source 290 may include one or more of, e.g., a medium-chain or long-chain fatty acid, for example, a long-chain polyunsaturated fatty acid ("LC-PUFA") triglyceride. Exemplary fats (e.g., lipids) in lipid source 290 may include natural or structured lipids, or omega-3 or omega-6 fatty acids, like docosahexaenoic acid ("DHA"), eicosapentaenoic acid ("EPA"), alpha-linolenic acid ("ALA"), arachidonic acid ("ARA" or "AA"), and/or linoleic acid ("LA"). Any suitable combination of lipids may be included in lipid source 290.

In some embodiments, lipid source 290 may be in the form of fish oil. In other embodiments, lipid source 290 may be from a plant source alone or in combination with fish oil. In other examples, lipid source 290 may be in the form of supplemental oils and/or infant fortifiers that may be used to supplement mother's breast milk, donor breast milk, and/or infant formulas. Examples of infant fortifiers include Similac® and Prolacta® fortifiers. Other examples of lipid sources may include a mixture of an infant fortifier with DHA and/or ARA and/or any other type of natural or structured lipid. Lipids contained in vessel 280 may be duplicative of those already in nutritional formula 110 or may not be present in nutritional formula 110 at all, or the lipids contained in vessel 280 may be a combination thereof.

In some embodiments, vessel 280 may be refillable or may be a single-use container and may be pre-filled or may need to be filled prior to and/or during use. A refillable vessel 280 may be refillable prior to, during, and/or after use. If vessel 280 is refillable, it may have an inlet (not shown), e.g., a re-sealable inlet, and/or may be configured to removeably connect to chamber 222. In some embodiments, a user (e.g., healthcare provider, patient, patient guardian, pharmacist, or other user) may attach vessel 280 to chamber 222 prior to use. For example, the user may select a pre-filled vessel 280 containing the desired lipid source 290 and may attach vessel 280 to chamber 222 for use. In some embodiments, vessel 280 may be pre-filled, and a user may select between different types of lipids or combinations of lipids and/or may select between different volumes of lipids, depending, e.g., on the needs of the patient. In such embodiments, vessel 280 may have a sealed opening that is either unsealed prior to attachment to chamber 222, or the action of attaching vessel 280 to chamber 222 may break the seal (e.g., perforate, puncture, displace, or otherwise open the seal). In some embodiments, a valve or other mechanical structure may be used to maintain lipid source 290 in vessel 280 prior to use and/or to control the flow of lipid source 290 out of vessel 280 and into chamber 222. In still other embodiments, a user may fill vessel 280 with the desired type of lipids, combination of lipids, and/or desired volume of lipids prior to and/or during use.

In some embodiments, vessel 280 and/or lipid source 290 may be mixed, heated, cooled, agitated, or otherwise prepared before use. For example, in some embodiments, one or more lipids and one or more fortifiers may be mixed together to form lipid source 290, multiple types of lipids may be mixed together to form lipid source 290, or multiple types of fortifiers may be mixed together to form lipid source 290, which may then be attached to chamber 222 for hydrolyzation. In other embodiments, lipid source 290 may include one type of lipid, multiple types of lipids, one type of fortifier, or multiple types of fortifiers, which may be attached to chamber 222 for hydrolyzation. Once prepared (if preparation is necessary), vessel 280 may be attached to chamber 222 for use.

In other embodiments, vessel 280 may not be detachable from chamber 222, and vessel 280 may be filled/re-filled while attached to chamber 222 or may come pre-filled and may not be refillable. In some such embodiments, a user may select between devices 210 prefilled with different lipids, combinations of lipids, and/or volumes of lipids prior to use.

In some embodiments, device 201 may include one or both of an inlet filter 250 and/or an outlet filter 260. Although both an inlet and an outlet filter are depicted in FIG. 2 for convenience, it is contemplated that only one filter may be included in device 201, or, in some embodiments, no filter may be included. Inlet filter 250 may be located at inlet 212 of chamber 222, and outlet filter 260 may be located at outlet 230 of chamber 222. In some embodiments, inlet filter 250 and outlet filter 260 may cooperatively define chamber 222 while in some embodiments, either or both of inlet filter 250 and outlet filter 260 may be located within or outside of chamber 222. For example, there may be a floor and a ceiling that cooperatively define chamber 222. The floor and ceiling may define one or more openings at the top and bottom of chamber 222 and/or they may be porous to allow lipids to pass into and out of chamber 222. Inlet filter 250 may be located above an opening in the ceiling of chamber 222 adjacent inlet 212 and/or outlet filter 260 may be located below an opening in the floor of chamber 222 adjacent outlet 230. In some embodiments, inlet filter 250 may be located below a ceiling within chamber 222 and/or outlet filter 260 may be located above a floor within chamber 222, or any combination of positions thereof. Inlet filter 250 and outlet filter 260 may prevent particles 300 (or other structures to which lipase may be immobilized) from exiting chamber 222 of device 201. Additionally or alternatively, the filters may prevent foreign objects from entering chamber 222, vessel 280, and/or enteral tube 124. This may be convenient, for example, if vessel 280 is refillable and/or does not come pre-filled and/or is detachable from chamber 222. Particles 300 (or other structures on which lipase may be immobilized) may be located between inlet filter 250 and outlet filter 260 (in embodiments in which two filters are used). Inlet filter 250 and outlet filter 260 may retain particles 300 within chamber 222 as lipid source 290 flows through device 201. In some embodiments, pore openings in inlet filter 250 and/or outlet filter 260 may aid in the emulsification and breakdown of fats from lipid source 290 as lipid source 290 flows through.

In one exemplary embodiment, body 210 of device 201 is made of a clear plastic or glass so that the plurality of particles 300 inside chamber 222 of body 210 are visible to the user. In some instances, this may allow the user to ensure proper flow through device 201, for example, by visual inspection. In other embodiments, chamber 222 may be opaque or may be made of any suitable material. Particles 300 contained in device 201 have lipase immobilized on their surfaces, and as lipid source 290 flows through chamber 222 and particles 300, the immobilized lipase hydrolyzes the fats and triglycerides, including triglycerides having LC-PUFAs (if included) in lipid source 290, breaking them down into monoglycerides and free fatty acids. After lipid source 290 flows through chamber 222 and particles 300, hydrolyzing fats and triglycerides, the hydrolyzed lipid source flows into a nutritional formula 110, such as mother's breast milk, donor breast milk, infant formula, or any suitable type of nutritional formula 110, to supplement the nutritional formula.

Lipid source 290 may flow through device 201 in any suitable manner. In some embodiments, device 201 may gravity-feed lipid source 290 through chamber 222, where lipid source 290 is hydrolyzed, and then hydrolyzed lipids 275 may flow into a nutritional formula 110 under the force of gravity. In some embodiments, fluidly connecting device 201 to a feeding system (for example systems 100 of FIGS. 1A and 1B) may promote the flow of lipid source 290 out of vessel 280, through chamber 222, and out of interface 223 (if included). For example, the flow of lipid source 290 out of vessel 280 may be driven by a pressure differential. The flow of nutritional formula 110, which may be in fluid communication with lipid source 290, may cause a decrease in pressure relative to lipid source 290 in vessel 280, which may in turn cause lipid source 290 to be drawn through chamber 222 and into the flow of nutritional formula 110, according to Bernoulli's principle. In such embodiments, an air vent may be included in vessel 280 and/or vessel 280 may be compressible so that it may collapse in on itself as lipid source 290 is drawn out of vessel 280. In other embodiments, vessel 280 may be sealed except for the opening fluidly connected to chamber 222. In some embodiments, lipid source 290 may be stored under pressure in vessel 280.

In some embodiments, vessel 280 or portions of vessel 280 may be deformable. A user may squeeze vessel 280, forcing lipid source 290 out of vessel 280 and into chamber 222. The vessel or portions of vessel 280 may deform as flow evacuates lipid source 290, for example, driven via a pressure differential. In some embodiments, a motorized compression roller or other mechanical device may be included and may compress vessel 280 in a controlled manner at a given rate or over a given amount of time. In some embodiments, a pump, e.g., a continuous or peristaltic pump (which may be manually operated or electronic), may be included in device 201 or attached to vessel 280 to urge lipid source 290 out of vessel 280. In other embodiments, a source of negative pressure may be connected to chamber 222, creating a vacuum into which a flow of lipid source 290 may be drawn. In some embodiments, the flow of nutritional formula 110 may draw lipid source 290 out of vessel 280, thereby causing it to mix into nutritional formula 110.

To facilitate the emptying of vessel 280, vessel 280 may include a valve or other flow-control device and/or may include an air release to equalize pressure as lipid source 290 is emptied from vessel 280. In some embodiments, vessel 280 may include measurement lines so that a user may observe how much of lipid source 290 has been released into nutritional formula 110 and/or how much lipid source 290 remains in vessel 280. In some embodiments, a syringe or other delivery device may feed lipid source 290 into vessel 280 either prior to and/or during use of device 201, and lipid source 290 may then flow into chamber 222. In some embodiments, a vibrating motor may be included in or attached to device 201 to vibrate device 201, agitate lipid source 290 and/or chamber 222, promote mixing of lipid source 290 with the lipase, assist the flow of lipid source 290 through chamber 222 and/or the flow of hydrolyzed lipids 275 into nutritional formula 110, and/or to assist with mixing of hydrolyzed lipids 275 into nutritional formula 110.

In some embodiments, some or all of lipid source 290 may pass into chamber 222 and may remain in chamber 222 for a period of time (i.e., a residence time) to prolong exposure of lipid source 290 to lipase to allow hydrolysis to occur. For example, a user may partially squeeze or otherwise deliver lipid source 290 from vessel 280 into chamber 222, then may wait for a period of time equal to the desired residence time, and then may continue to squeeze or otherwise finish deploying lipid source 290 from vessel 280. In some aspects, vessel 280 may contain air or some other non-lipid fluid, and lipid source 290 may first be delivered from vessel 280 into chamber 222 upon a first compression (or other delivery method), and then after the residence period, a second compression (or other delivery method) may deliver air or other fluid from vessel 280 into chamber 222 to expel hydrolyzed lipid source 290 from chamber 222 and into nutritional formula 110. Accordingly, delivery of lipid source 290 through chamber 222 and into nutritional formula 110 may be a multi-step process. In still other embodiments, device 201 may be configured so that lipid source 290 passes slowly through chamber 222 so that lipid source 290 remains in chamber 222 for at least the duration of a desired residence time. For example, chamber 222 may be filed with particles 300 of a certain size and/or density so as to slow the passage of lipid source 290 through chamber 222, or a valve may be used to maintain lipid source 290 within chamber 222 for the duration of the residence time. In such embodiments, a vibrating motor may be included in or attached to device 201 to vibrate chamber 222 when lipid source 290 is contained within chamber 222 (e.g., during the residence time) to promote mixing of lipid source 290 with lipase. Residence time may be, for example, 5 seconds, 10 seconds, 20 seconds, 30 seconds, 45 seconds, 1 minute, 2 minutes, 3 minutes, 4 minutes, 5 minutes, 10 minutes, 20 minutes, 30 minutes or more than 30 minutes.

As shown in FIG. 2, in some embodiments, particles 300 may be formed as substantially spherical beads. In other embodiments, particles 300 may be randomly shaped or irregular particles, or may be elliptical, oblong, donut-shaped, a prism, polygonal, elongated, or any other suitable shape or shapes. Particles 300 may have a smooth or a textured surface. Particles 300 may be shaped to increase or decrease their surface area. Particles 300 may be formed of individual particles, which may each have substantially the same shape and/or surface or may have two or more different shape and/or surface combinations. Particles 300 may be formed of any suitable material, and lipase may be immobilized on particles 300 in any suitable manner, e.g., via adsorption, ionic binding, covalent binding, cross-linking, encapsulation, and/or entrapment. Lipases may be immobilized on or in particles 300 found within the chamber 222 such that the lipases are in fluid contact with lipid source 290 as lipid source 290 flows through chamber 222.

While particles 300 are depicted in the exemplary figures, it is appreciated that lipase may be immobilized in chamber 222 in any suitable manner. For example, lipases may be immobilized or contained within structures located inside chamber 222, such as beads, rods, projections extending from portions of chamber 222, or other suitable structures. In some embodiments, lipases may be immobilized on or contained within a wall of chamber 222, and/or may be immobilized on one or more filters included in device 201.

It is also contemplated that, in some embodiments, lipase may not be immobilized and may simply be contained within chamber 222 or within a portion of chamber 222. In some such embodiments, one or more filters may keep the free (i.e., not immobilized) lipase within chamber 222 and/or device 201.

As lipid source 290 flows into chamber 222, lipid source 290 comes into contact with the lipase contained within chamber 222, and the lipids are hydrolyzed, e.g., into monoglycerides and free fatty acids. The lipase (immobilized or free) may be located along the flow path of lipid source 290 as it flows out of vessel 280 and through chamber 222. After lipid source 290 comes into contact with the lipase, hydrolyzed lipids 275 are fed into nutritional formula 110, such as, e.g., mother's milk, donor milk, or infant formula. After introduction of the hydrolyzed lipids into nutritional formula 110, supplemented nutritional formula 111 may be fed to a patient.

Lipase included in the devices herein may cleave two out of three bonds in a triglyceride, i.e., at the sn-1 and sn-3 positions, leaving an sn-2 monoglyceride. Exemplary lipases may be obtained from animals, plants, and from many natural or genetically engineered microorganisms. In some embodiments, the lipase may include one or more of, e.g., a *Chromobacterium viscosum, Pseudomonas fluorescens, Burcholderia cepacia*, or *Rhizopus oryzae* lipase, or any other suitable wild-type or recombinant lipase or combination thereof.

FIG. 3 through FIGS. 12A and 12B illustrate various devices and exemplary ways to incorporate these devices into feeding systems, according to embodiments of the present disclosure.

Device 201 may be configured to treat patients with lipase deficiencies and/or malabsorption. Device 201 may be used instead of, or in addition to, other treatments, such as the use of device 200 shown in FIG. 1B, to provide an increased concentration of hydrolyzed lipids to nutritional formula 110. Device 201 may be used as a point-of-care device, such as added to a syringe of mother's milk (shown in FIGS. 9A and 9B) or other nutrient source. Device 201 may be used with hydrolyzed nutritional formula 110, such as nutritional formula 110 that has already been treated with device 200 discussed herein above, or may be used by itself to add hydrolyzed lipids to nutritional formula, e.g., without the use of device 200.

Figure 3:
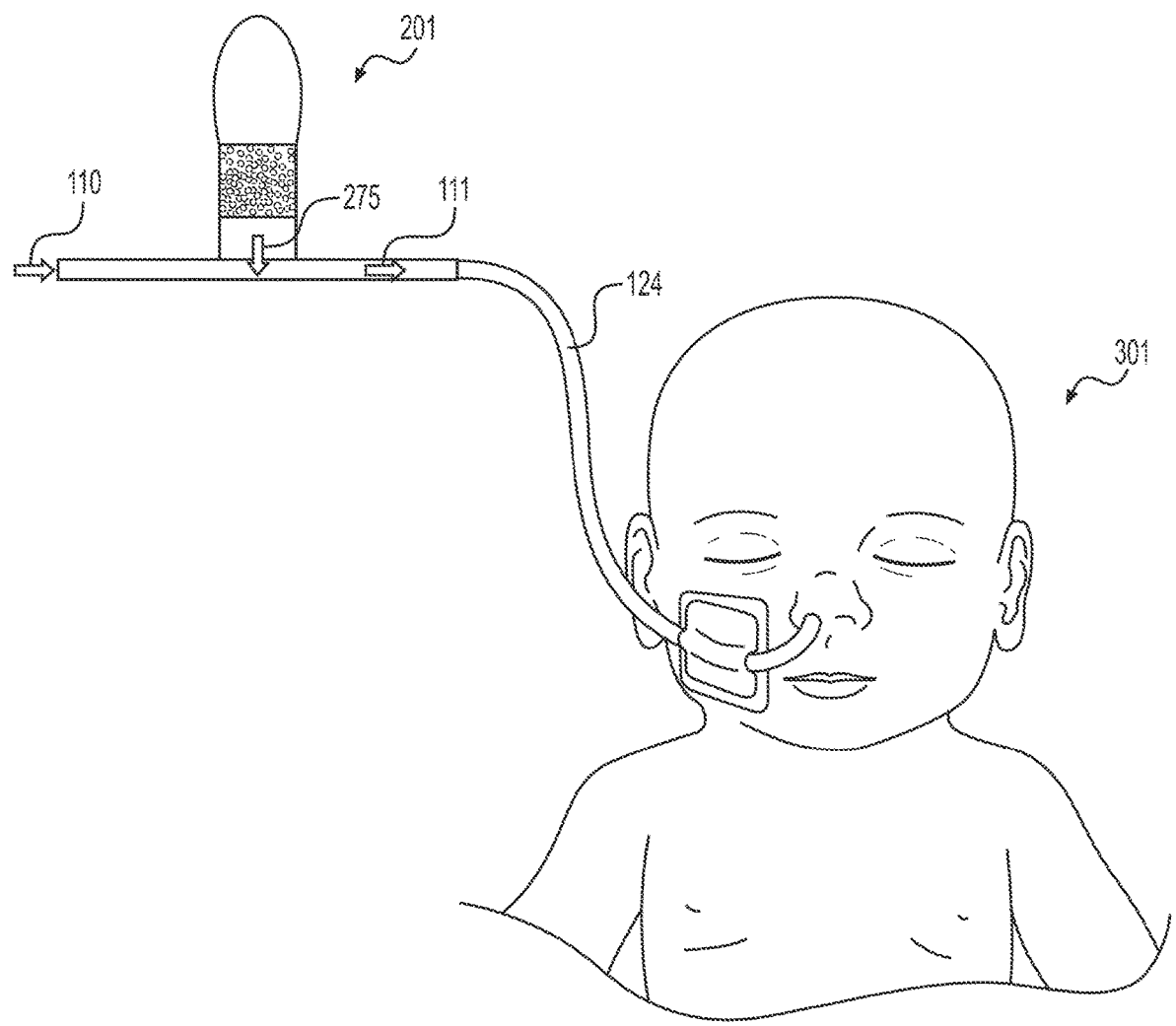
FIG. 3 illustrates a feeding system of which the device of FIG. 2 may be a part, according to embodiments of the present disclosure.

FIG. 3 shows device 201 arranged in-line with an enteral tube 124 supplying nutritional formula 110 to an infant patient 301. The flow of nutritional formula 110 through a proximal portion of enteral tube 124 (not shown) and the flow of supplemented nutritional formula 111 may be controlled by any of the mechanisms previously discussed in relation to system 100, e.g., by gravity or via a pump or syringe. As discussed above, device 201 may be used to supplement nutritional formula 110 with hydrolyzed lipids as lipids are passed from lipid source 290, through chamber 222, and into nutritional formula 110 being fed to patient 301 through enteral tube 124. Since hydrolyzed lipids have a short shelf-life, a point-of-care configuration, such as the one depicted in FIG. 3, may be advantageous to avoid hydrolyzed lipid degradation prior to feeding the patient.

Figure 4:
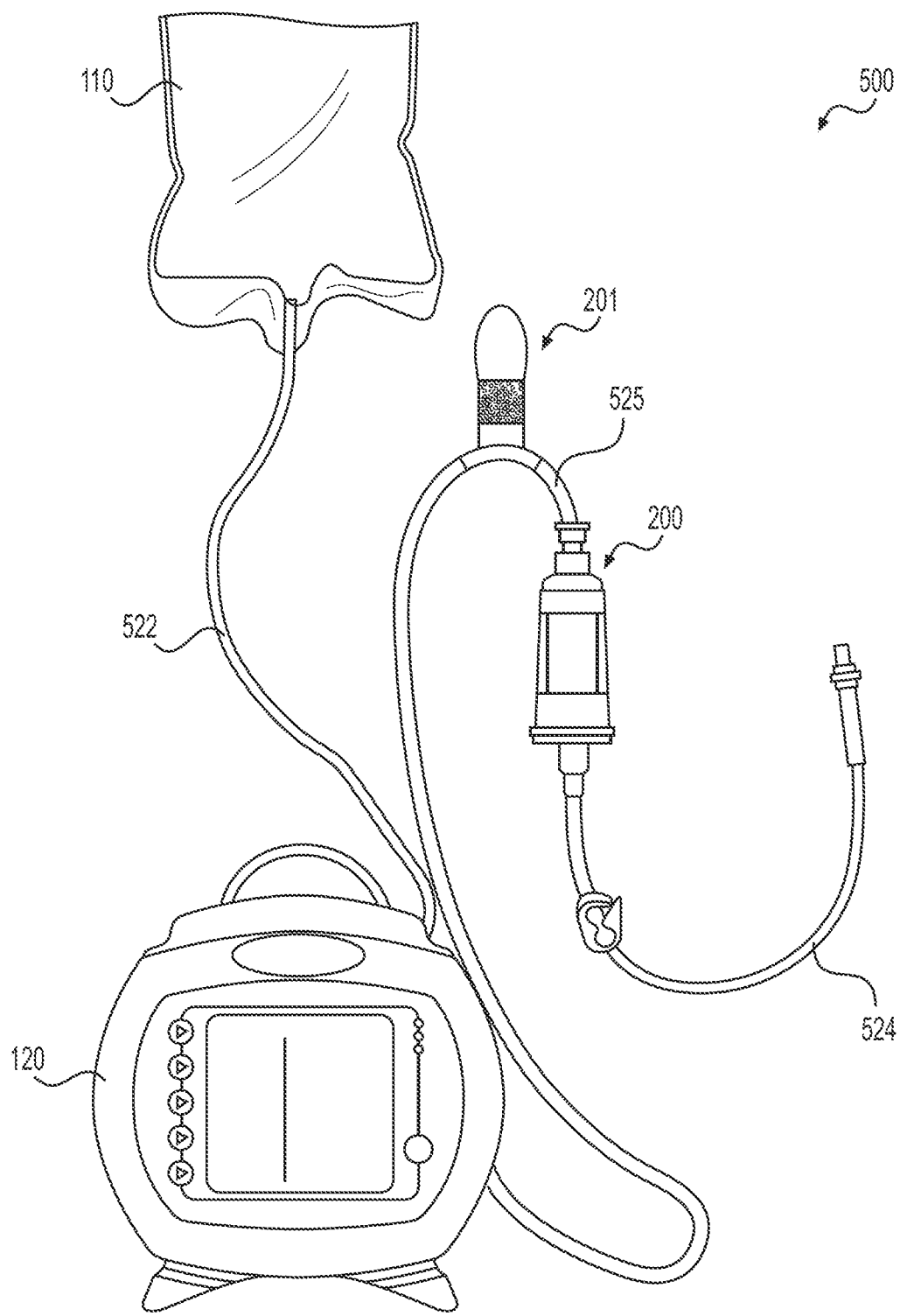
FIG. 4 illustrates a feeding system including an exemplary device for supplementing a nutritional formula, according to embodiments of the present disclosure.

FIG. 4 shows an exemplary application of device 201. Feeding system 500 may be substantially the same as feeding system 100 of FIG. 1B, with the addition of device 201. Feeding system 500 may be used in combination with device 200 for feeding a nutritional formula 110 further supplemented with hydrolyzed lipids using device 201. For example, hydrolyzed lipids from device 201 may be introduced into nutritional formula 110, and any lipids already present in nutritional formula 110 may be hydrolyzed using device 200, all prior to administration of supplemented and hydrolyzed nutritional formula to a subject via a feeding tube 524. System 500 may include a fat hydrolysis device 200, a pump 120, and a tube 522 fluidly connecting a source of nutritional formula 110 to device 201. Nutritional formula 110 may be flowed from the source, through tube 522, to device 201 for supplementation. As nutritional formula 110 flows past device 201, device 201 may deliver hydrolyzed lipids to nutritional formula 110, increasing the concentration of lipids in nutritional formula 110. From device 201, nutritional formula 110 may then flow to device 200, where the supplemented nutritional formula may be exposed to lipase in order to hydrolyze any lipids in nutritional formula 110. Device 200 may also hydrolyze any lipids from device 201 that may have exited device 201 without having been hydrolyzed by the lipase in chamber 222 (e.g., if device 201 has less than 100% efficiency). System 500 may also include a tube 525 having an end configured to connect to device 201 and an opposite end configured to connect to device 200 for flowing supplemented nutritional formula from device 201 to device 200. System 500 may further include a tube 524 having an end configured to connect to device 200 and an opposite end configured to connect to a patient to deliver processed and supplemented nutritional formula 110 from device 200 to the patient for ingestion. Although tubes 522, 524, and 525 are described as separate tubes, it is possible that additional tubes may be used in system 500 or that the element numbers may reference different sections of the same tube.

Although device 201 is depicted as being connected to feeding system 500 downstream of pump 120, in some exemplary embodiments, device 201 may be connected to tube 522 upstream of pump 120. In some embodiments, the pumping force may be comparatively stronger upstream of pump 120, causing a faster flow of nutritional formula through the portion of tubing connecting the source of nutritional formula 110 to pump 120. Locating device 201 upstream of pump 120 may allow device 201 to take advantage of the stronger pumping force and faster flow to draw lipids in device 201 from the lipid source, through the lipase, and out of device 201.

Figure 5:
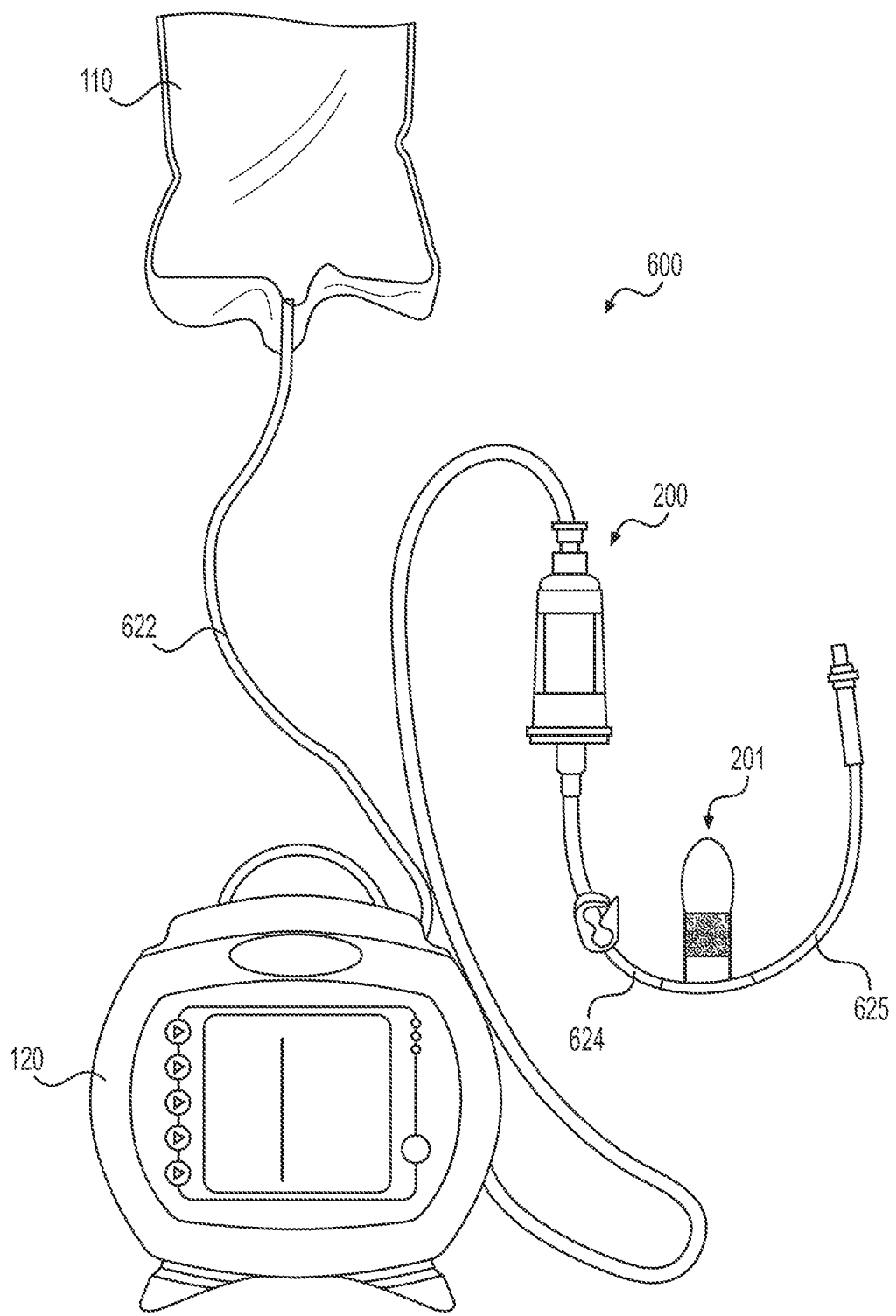
FIG. 5 illustrates a feeding system including an exemplary device for supplementing a nutritional formula, according to embodiments of the present disclosure.

FIG. 5 shows another exemplary application of device 201. Feeding system 600 may be substantially the same as feeding system 500, except for the positioning of device 201. Feeding system 600 includes tube 622 fluidly connecting a source of nutritional formula 110 to device 200 and a tube 624 fluidly connecting device 200 to device 201. Accordingly, lipids already present in nutritional formula 110 may be passed through device 200 and hydrolyzed by device 200, and then the hydrolyzed nutritional formula may be flowed from device 200 to device 201 for delivery of additional hydrolyzed lipids into the nutritional formula. System 600 may further include a tube 625 having an end configured to connect to device 201 and an opposite end configured to connect to a patient to deliver processed and supplemented nutritional formula from device 201 to the patient for ingestion. Although tubes 622, 624, and 625 are described as separate tubes, it is possible that additional tubes may be used in system 600 or that the element numbers may reference different sections of the same tube.

Figure 6:
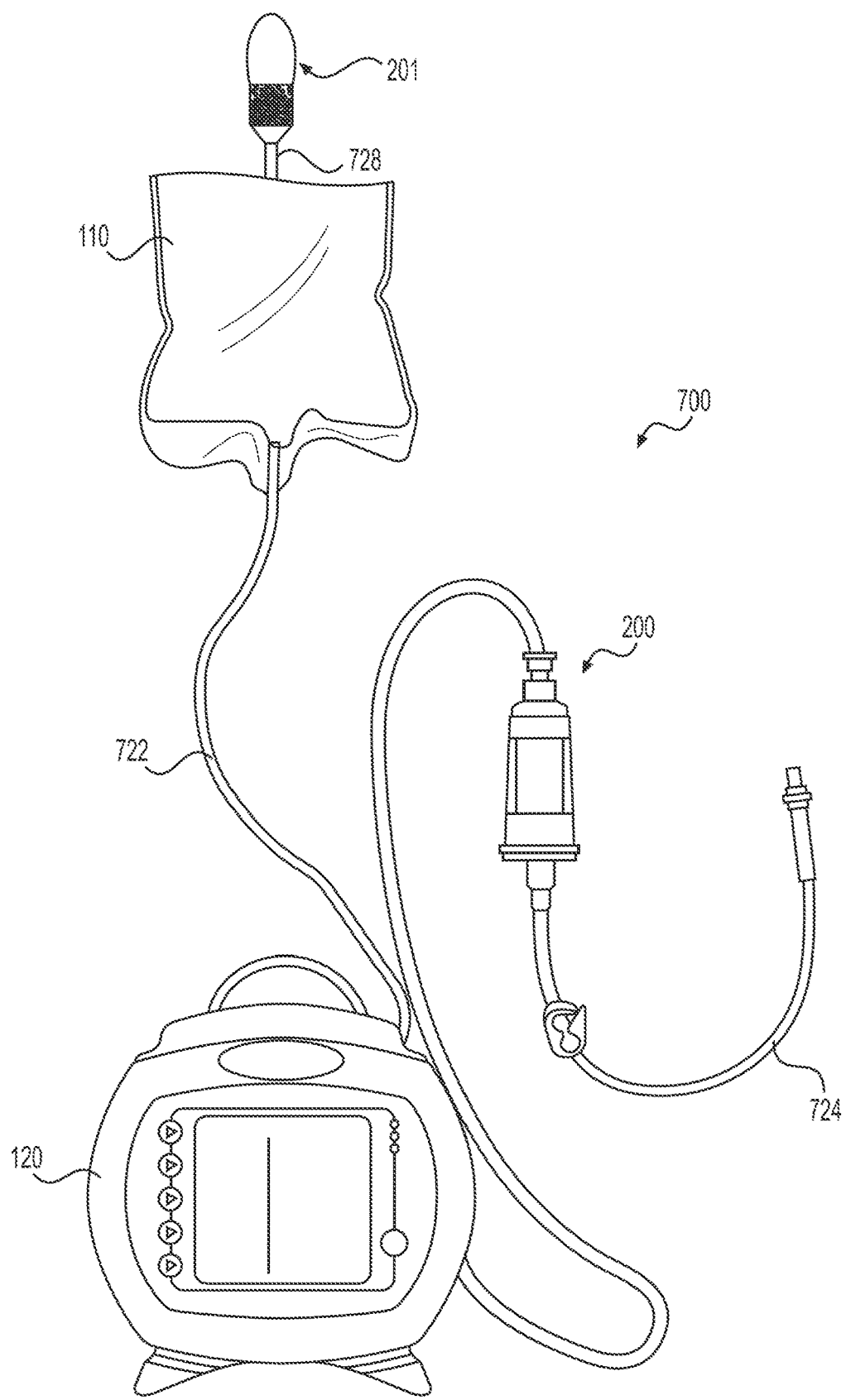
FIG. 6 illustrates a feeding system including an exemplary device for supplementing a nutritional formula, according to embodiments of the present disclosure.

FIG. 6 shows another exemplary application of device 201. Feeding system 700 may be substantially the same as feeding systems 500 and 600 except for the positioning of device 201. Feeding system 700 includes a tube 728 fluidly connecting device 201 with a source of nutritional formula 110 so that hydrolyzed lipids are introduced from device 201 directly into the source of nutritional formula. Alternatively, hydrolyzed lipids may be added to a container configured to hold the source of nutritional formula 110 first, and then nutritional formula 110 may be added to the container. It should also be recognized that device 201 may be replaced with any other suitable embodiment of device described herein.

With device 201 arranged in this location, supplemented nutritional formula is flowed through tube 722, which connects the source of nutritional formula 110, already supplemented with hydrolyzed lipids by device 201, to device 200, where lipids in the supplemented nutritional formula are further hydrolyzed. The hydrolyzed and supplemented nutritional formula is then flowed through tube 724, which has an end configured to connect to device 200 and an opposite end configured to connect to a patient to deliver hydrolyzed and supplemented nutritional formula 110 from device 200 to the patient for ingestion. Although tubes 722 and 724 are described as separate tubes, it is possible that additional tubes may be used in system 700 or that the element numbers may reference different sections of the same tube. In some aspects, device 201 may be used to supplement nutritional formula 110, and then supplemented nutritional formula 110 may then be placed in fluid communication with tube(s) 722, 724 to provide supplemented nutritional formula to a subject. In other words, a healthcare provider or subject may use device 201 to introduce hydrolyzed lipids into nutritional formula 110 and then may attach nutritional formula 110 to system 700 and/or assemble system 700.

Figure 7:
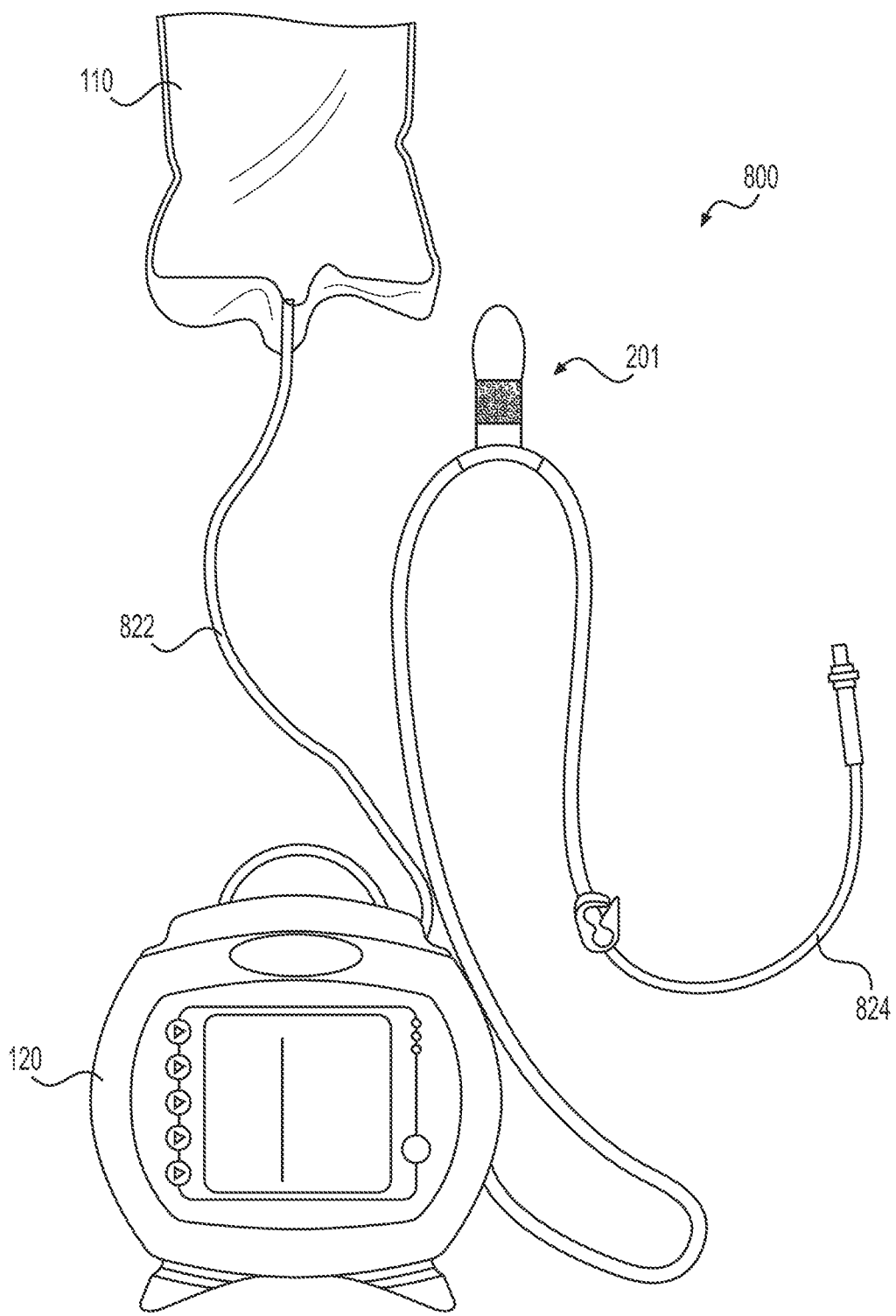
FIG. 7 illustrates a feeding system including an exemplary device for supplementing a nutritional formula, according to embodiments of the present disclosure.

FIG. 7 shows an exemplary application of device 201 substantially similar to the systems of FIGS. 4 and 5, except without the use of device 200. Specifically, FIG. 7 shows a feeding system 800 including a source of nutritional formula 110, a tube 822, pump 120, device 201, and a tube 824. Tube 822 fluidly connects the source of nutritional formula 110 with device 201 for flowing nutritional formula 110 to device 201, where device 201 supplements nutritional formula 110 with hydrolyzed lipids. System 800 may also include a tube 824 having an end configured to connect to device 201 and an opposite end configured to connect to a patient to deliver supplemented nutritional formula 110 from device 201 to the patient for ingestion. Although tubes 822 and 824 are described as separate tubes, it is possible that additional tubes may be used in system 700 or that the element numbers may reference different sections of the same tube.

Although device 201 is depicted as being connected to feeding system 800 downstream of pump 120, in some exemplary embodiments, device 201 may be connected to tube 822 upstream of pump 120. In some embodiments, the pumping force may be comparatively stronger upstream of pump 120, causing a faster flow of nutritional formula through the portion of tubing connecting the source of nutritional formula 110 to pump 120. Locating device 201 upstream of pump 120 may allow device 201 to take advantage of the stronger pumping force and faster flow to draw lipids in device 201 from the lipid source, through the lipase, and out of device 201.

Figure 8:
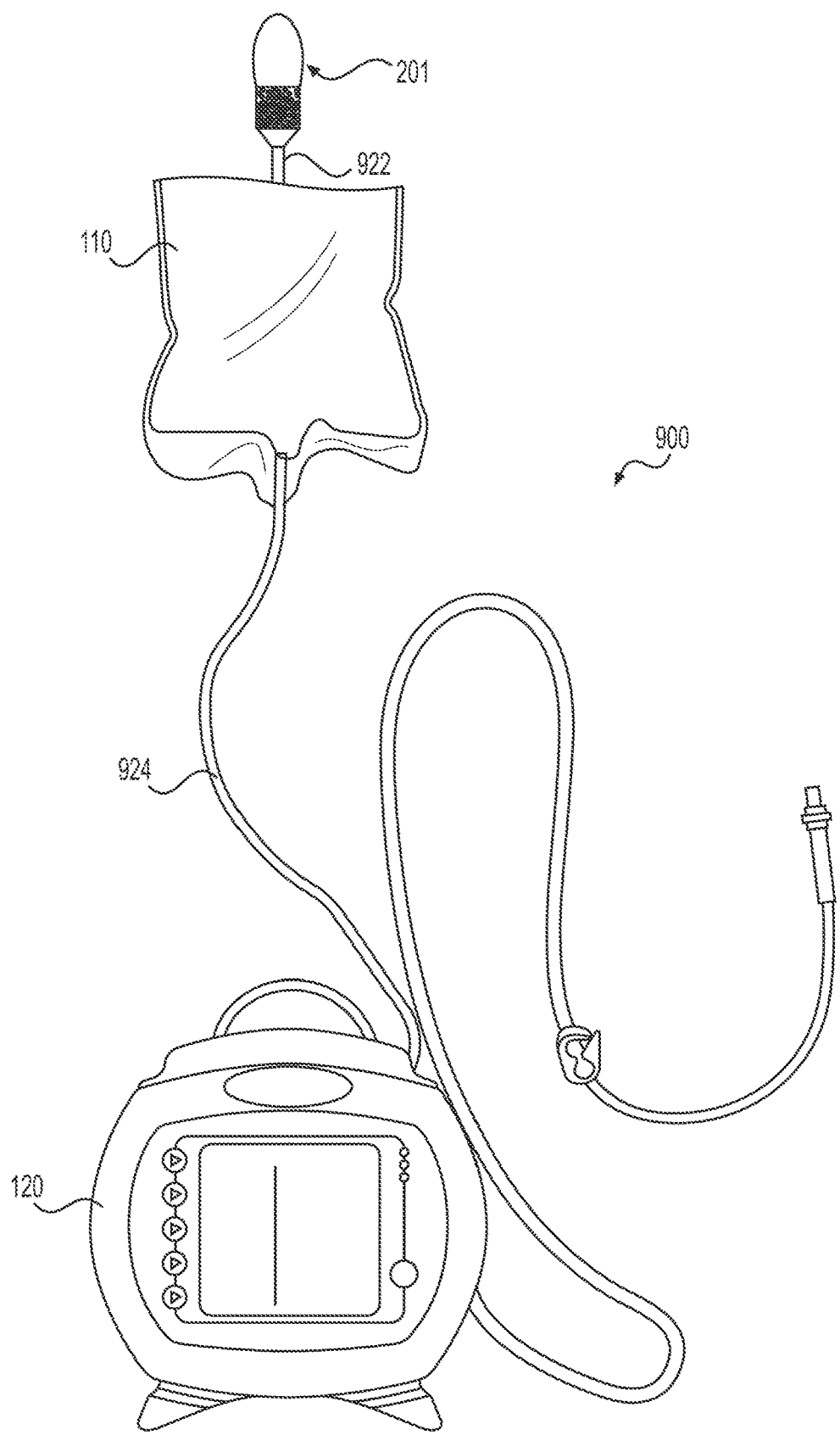
FIG. 8 illustrates a feeding system including an exemplary device for supplementing a nutritional formula, according to embodiments of the present disclosure.

FIG. 8 shows an additional exemplary application of device 201 substantially similar to the system of FIG. 7, except with device 201 positioned at the source of nutritional formula 110. Specifically, FIG. 8 shows a feeding system 900 including a source of nutritional formula 110, a tube 922, a tube 924, pump 120, and device 201. Tube 922 fluidly connects device 201 with the source of nutritional formula 110 so that hydrolyzed lipids are introduced from device 201 directly into the source of nutritional formula. Alternatively, hydrolyzed lipids may be added to a container configured to hold the source of nutritional formula 110 first, and then nutritional formula 110 may be added to the container. It should also be noted that device 201 may be replaced with any other suitable embodiment of device described herein. Tube 924 includes an end configured to connect to the source of nutritional formula 110 and an opposite end configured to connect to a patient to deliver supplemented nutritional formula 110 from the source to the patient for ingestion. Although tubes 922 and 924 are described as separate tubes, it is possible that additional tubes may be used in system 900 or that the element numbers may reference different sections of the same tube. In some aspects, device 201 may be used to supplement nutritional formula 110, and then supplemented nutritional formula 110 may then be placed in fluid communication with tube 924 to provide supplemented nutritional formula to a subject. In other words, a healthcare provider or subject may use device 201 to introduce hydrolyzed lipids into nutritional formula 110 and then may attach nutritional formula 110 to system 900 and/or assemble system 900.

FIG. 9A shows another exemplary embodiment of the present disclosure. Device 401 may include any of the previously described elements of device 201, which may operate in a similar manner. Device 401 may include a vessel 480 containing lipid source 290, a chamber 422 containing particles 410, and an output assembly 430. Device 401 may be used to introduce hydrolyzed lipids 475 into a source of nutritional formula 110, such as into a syringe 450 containing nutritional formula 110. For example, a user may uncap, unseal, break a rupturable seal, or otherwise open an outlet in output assembly 430 to allow hydrolyzed lipids 475 to exit device 401. Once device 401 is uncovered and ready for use, a user may squeeze vessel 480 (if deformable) to expel lipid source 290 out of vessel 480, through chamber 422 where the lipids are hydrolyzed, and out of output assembly 430. A flow path may extend from an opening in vessel 480, through chamber 422, and through output assembly 430, along which lipid source 290 may flow through device 401 when released from vessel 480. immobilized lipase may be located in chamber 422 within the flow path so that the lipase hydrolyzes lipid source 290 as it flows through chamber 422. In some embodiments, a vent opening in vessel 480 may also be uncovered in order to promote the release of lipid source 290 out of vessel 480. In other embodiments, vessel 480 may only include one opening—the opening in fluid communication with chamber 422.

Once hydrolyzed lipids 475 are introduced into syringe 450, a plunger 414 may be coupled to syringe 450, and syringe 450 may be ready to deliver supplemented nutritional formula 111 to a patient, as shown in FIG. 9B. FIG. 9B shows a syringe filled with supplemented nutritional formula 111 supplemented with hydrolyzed lipids 475 from device 401.

In some embodiments, syringe 450 may be filled by attaching device 401 to a distal end of syringe 450. For example, plunger 414 may not be removed from syringe 450, and, instead, output assembly 430 may be fluidly connected to a distal end of syringe 450 (opposite plunger 414). Output assembly 430 may be connected to syringe 450 via a snap-fit, twist-fit, friction-fit, threaded, Luer-lock, or any other suitable connection. Once device 401 is connected to a distal end of syringe 450, plunger 414 may be drawn back, creating a negative pressure in syringe 450. This negative pressure may draw lipid source 290 out of vessel 480, through chamber 422, and may draw hydrolyzed lipids 475 into syringe 450. In this way, hydrolyzed lipids may be introduced into syringe 450 without breaking sterility. Nutritional formula 110 may already be present in syringe 450 when hydrolyzed lipids 475 are drawn from device 401 into syringe 450, or nutritional formula 110 may be added to syringe 450 after hydrolyzed lipids 475 are drawn into syringe 450.

Syringe 450 may be used to administer supplemented nutritional formula 111 supplemented with hydrolyzed lipids 475 to a patient. In some embodiments, syringe 450 filled with supplemented nutritional formula 111 may be fluidly connected to any of feeding systems 100 to 900 described herein to deliver supplemented nutritional formula 111 to a patient. Device 401 may be used to prepare supplemented nutritional formula 111 supplemented with hydrolyzed lipids 475 for storage or for immediate administration to a patient. Device 401 may be used to introduce hydrolyzed lipids 475 from a lipid source 290 into nutritional formula in any form of container for use in feeding a patient.

For example, device 401 may be used to introduce hydrolyzed lipids 475 into a can 490 (FIG. 10A) or a bottle 495 (FIG. 10B). Bottle 495 may be a baby bottle or a water bottle. Although not specifically depicted, device 401 may be used to add hydrolyzed lipids 475 into any other suitable container, including, e.g., a cup, mug, blender, or juicer. As described above, a user may uncap, unseal, break a rupturable seal, or otherwise open an output in output assembly 430 to allow hydrolyzed lipids to exit 475. Once device 401 is uncovered and ready for use, a user may squeeze vessel 480 (if deformable) to expel lipid source 290 out of vessel 480, through chamber 422 where the lipids are hydrolyzed, and out of output assembly 430. In some embodiments, a vent opening in vessel 480 may also be uncovered in order to promote the release of lipid source 290 out of vessel 480.

In some embodiments, vessel 480 may be refillable or may be a single-use container and may be pre-filled or may need to be filled prior to and/or during use. A refillable vessel 480 may be refillable prior to, during, and/or after use. If vessel 480 is refillable, it may have an inlet (not shown), e.g., a re-sealable inlet, and/or may be configured to removeably connect to chamber 422. In some embodiments, a user (e.g., healthcare provider, patient, patient guardian, pharmacist, or other user) may attach vessel 480 to chamber 422 prior to use. For example, the user may select a pre-filled vessel 480 containing the desired lipid source 290 and may attach vessel 480 to chamber 422 for use. In some embodiments, vessel 480 may be pre-filled, and a user may select between different types of lipids or combinations of lipids and/or may select between different volumes of lipids, depending, e.g., on the needs of the patient. In such embodiments, vessel 480 may have a sealed opening that is either unsealed prior to attachment to chamber 422, or the action of attaching vessel 480 to chamber 422 may break the seal (e.g., perforate, puncture, displace, or otherwise open the seal). In some embodiments, a valve or other mechanical structure may be used to maintain lipid source 290 in vessel 480 prior to use and/or to control the flow of lipid source 290 out of vessel 480 and into chamber 422. In still other embodiments, a user may fill vessel 480 with the desired type of lipids, combination of lipids, and/or desired volume of lipids prior to and/or during use.

In some embodiments, vessel 480 and/or lipid source 290 may be mixed, heated, cooled, agitated, or otherwise prepared before use. For example, in some embodiments, one or more lipids and one or more fortifiers may be mixed together to form lipid source 290, multiple types of lipids may be mixed together to form lipid source 290, or multiple types of fortifiers may be mixed together to form lipid source 290, which may then be attached to chamber 422 for hydrolyzation. In other embodiments, lipid source 290 may include one type of lipid, multiple types of lipids, one type of fortifier, or multiple types of fortifiers, which may be attached to chamber 422 for hydrolyzation. Once prepared (if preparation is necessary), vessel 480 may be attached to chamber 422 for use.

In other embodiments, vessel 480 may not be detachable from chamber 422, and vessel 480 may be filled/re-filled while attached to chamber 422 or may come pre-filled and may not be refillable. In some such embodiments, a user may select between devices 401 prefilled with different lipids, combinations of lipids, and/or volumes of lipids prior to use.

In some embodiments, device 401 may be used to supplement a beverage other than a nutritional formula, for example, a soft drink, water, coffee, tea, juice, or any other suitable beverage. In such embodiments, the beverage may be poured into a container for the addition of hydrolyzed lipids 475 from device 401, or a can, bottle, carton, or other suitable container already containing the beverage may be opened, and device 401 may be used to introduce hydrolyzed lipids 475 directly into the original container.

Output assembly 430 of FIGS. 9A through 10B may be configured to attach to a container holding nutritional formula 110 to deliver hydrolyzed lipids 475 to nutritional formula 110, or output assembly 430 may be configured to deliver hydrolyzed lipids 475 while spaced apart from nutritional formula 110 and a container holding the nutritional formula. For example, some devices 401 may simply be held above an opening in the container so that hydrolyzed lipids 475 are delivered from output assembly 430 into the open container and into nutritional formula 110. Although output assembly 430 is depicted in the figures as being funnel-shaped and having an end connected to chamber 422 that is wider than an end through which hydrolyzed lipids 475 are output from device 401, it is contemplated that output assembly 430 may have any suitable shape or size.

Although the description of FIGS. 9A, 9B, 10A, and 10B above reference hydrolyzed lipids 475 being added to a syringe or other container containing nutritional formula 110, it is also contemplated that hydrolyzed lipids 475 may be added first to the syringe or container, and then nutritional formula 110 may be added to the syringe or container.

Figure 11A:
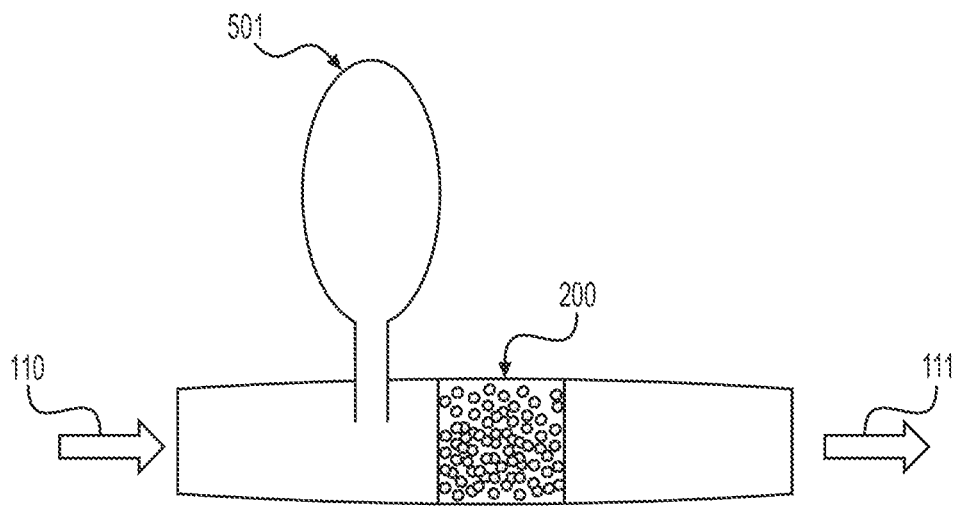
FIG. 11A illustrates an exemplary device for supplementing a nutritional formula, according to embodiments of the present disclosure.
Figure 11B:
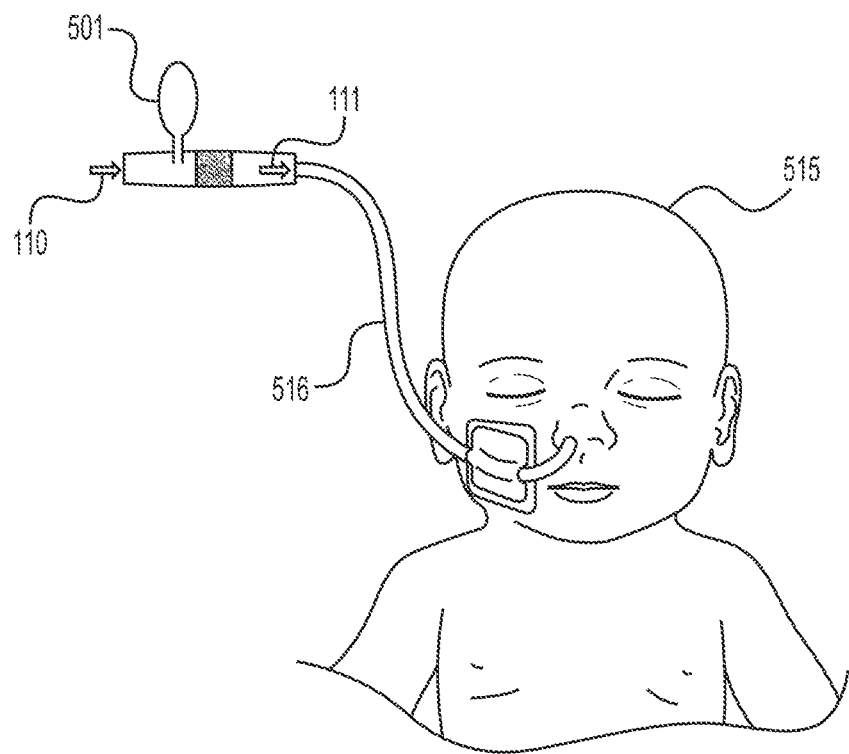
FIG. 11B illustrates a feeding system of which the device of FIG. 11A may be a part, according to embodiments of the present disclosure.

The embodiments of FIGS. 11A and 11B depict a slightly different variation of the devices described above for use with a feeding system like that of FIG. 1A. For example, a vessel 501 containing a source of lipids may be included upstream of device 200, which may be configured to hydrolyze nutritional formula 110 flowing through it. In this way, nutritional formula 110 may first be supplemented with un-hydrolyzed lipids from vessel 501, and then nutritional formula 110 supplemented with the additional lipids may together be flowed through device 200. Accordingly, device 200 may hydrolyze the lipids introduced by vessel 501 into the flow of nutritional formula 110, as well as any lipids that may have already been present in nutritional formula 110. Hydrolyzed, supplemented nutritional formula 111 may then flow out of device 200. For example, as is shown in FIG. 11B, hydrolyzed, supplemented nutritional formula 111 may be flowed into a feeding tube 516 to provide a nutritional formula containing pre-hydrolyzed lipids to a patient 515.

Although vessel 501 is depicted as being immediately upstream of device 200, it is contemplated that vessel 501 may be included in any suitable location upstream of device 200. Further, a source of lipids contained in vessel 501 may be driven out of device 501 in any of the ways described above in reference to devices 201 and/or 401.

Figure 12A:
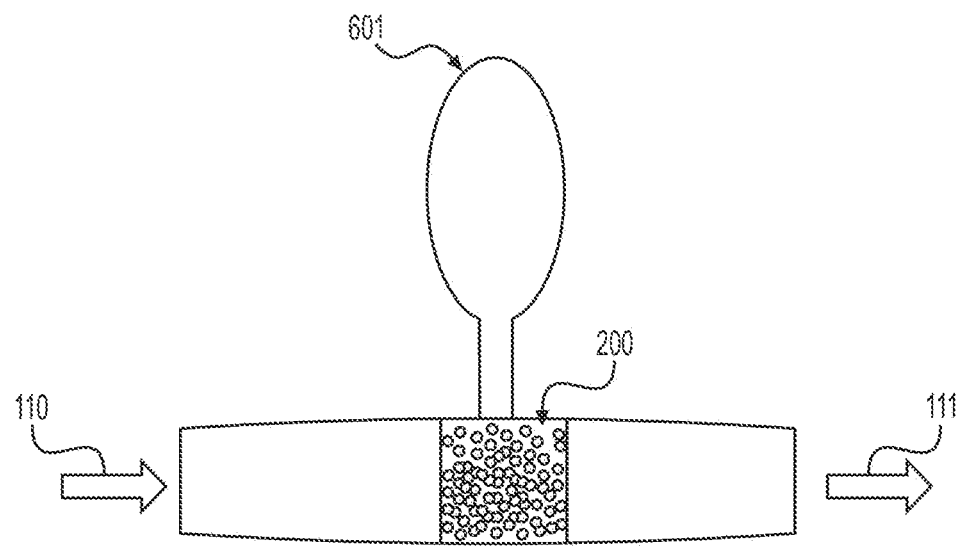
FIG. 12A illustrates an exemplary device for supplementing a nutritional formula, according to embodiments of the present disclosure.
Figure 12B:
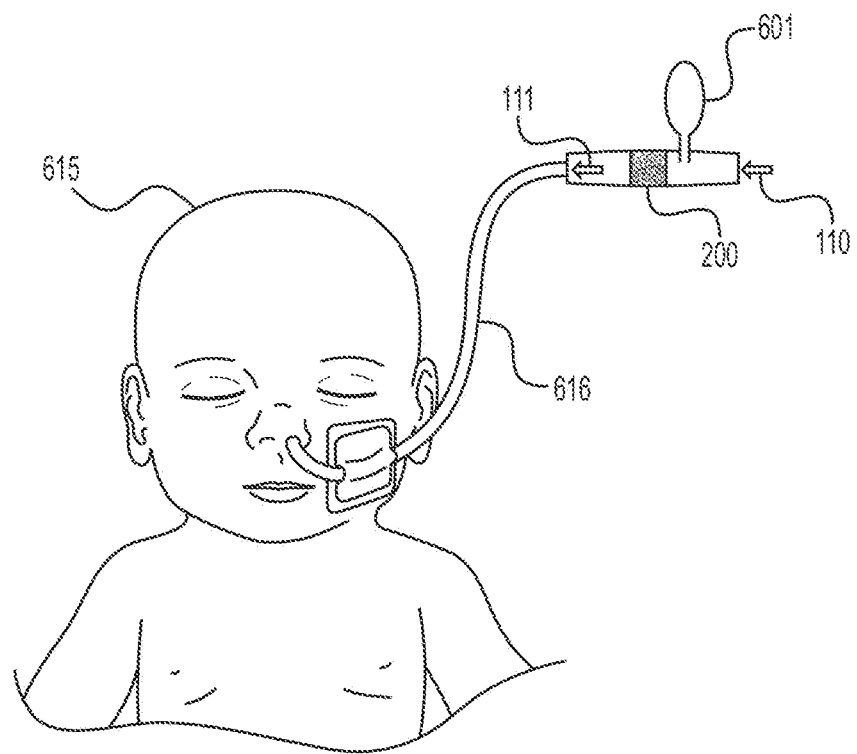
FIG. 12B illustrates a feeding system of which the device of FIG. 12A may be a part, according to embodiments of the present disclosure.

FIGS. 12A and 12B depict another exemplary embodiment in which lipids from a vessel 601 are added directly into device 200. Device 200, which may contain immobilized lipase and may be configured to hydrolyze lipids, may receive a flow of nutritional formula 110 via a first path and may receive a flow of lipids from vessel 601 via a second path. Whereas FIGS. 11A and 11B depict an embodiment in which nutritional formula is first supplemented with un-hydrolyzed lipid prior to passing through device 200, FIGS. 12A and 12B depict an embodiment in which nutritional formula 110 and lipids from vessel 601 are separately fed into device 200 via discrete paths. The lipids and nutritional formula 110 may be combined within device 200, as the lipids are hydrolyzed, and as any lipids already present in nutritional formula 110 are also hydrolyzed. Hydrolyzed nutritional formula supplemented with hydrolyzed lipids from vessel 601 may then exit device 200 along a combined flow path. For example, as is shown in FIG. 12B, hydrolyzed, supplemented nutritional formula 111 may be flowed into a feeding tube 616 to provide a nutritional formula containing pre-hydrolyzed lipids to a patient 615.

Lipids from vessel 601 may be drawn into device 200 and into the flow of nutritional formula 110 in any suitable manner described above in reference to devices 201 and/or 401.

Although FIG. 12A depicts a vessel 601 containing a source of lipids, it is contemplated that rather than being stored in a vessel, lipids may be directed into device 200 through a tube or via any other suitable source.

Numerous different aspects of devices 201 and 401 and vessels 501 and 601 have been described. Particular aspects include a vessel for containing a lipid source and an immobilized lipase enzyme configured to hydrolyze the lipids to supplement a nutritional formula. The supplementation of nutritional formula may promote the delivery of hydrolyzed fats (e.g., free fatty acids and/or monoglycerides) to the patient, for example, to the intestine (e.g., the small intestine) of a patient to promote the absorption of hydrolyzed fats by the body.

Use of the disclosed devices may provide one or more benefits. For example, surprisingly, it was found that when lipids were hydrolyzed in the presence of MCTs and/or l-Carnitine, there was an improvement in absorption of lipids and other nutrients by patients. As a result of this surprising finding, premature infants and other patients may be able to more efficiently absorb LCTs, as well as other fats, using embodiments of the disclosure.

Further, use of the devices may increase the number of total calories and/or energy obtained by a patient while keeping the volumes of nutritional formula ingested by the patient relatively low due to the increased density of nutrients of the nutritional formula consumed. For example, a larger volume of un-supplemented nutritional formula may need to be ingested in order to obtain the same nutrient amount as a smaller volume of nutritional formula supplemented with hydrolyzed lipids. Additionally, although device 200 may be able to hydrolyze lipids already present in a nutritional formula, it cannot increase the nutrient content of the nutritional formula—it can only make what is already present more available to the body for absorption by the body. Devices of the disclosure (e.g., devices 201 or 401) have the ability to not only provide lipids to a supplemented nutritional that are more biologically available, they also increase the overall concentration of lipids in the supplemented nutritional formula. This is useful, because, as described above, nutritional formula (e.g., mother's milk, donor milk, or infant formula or fortifiers) may not otherwise contain a high enough concentration of lipids or other nutrients.

Additionally, devices 201, 401 and vessels 501, 601 may be used to introduce lipids into a nutritional formula that are not otherwise found in a nutritional formula or are found only in lower concentrations. For example, nutritional formulas that already contain certain lipids, e.g., DHA or EPA, may be more expensive than other nutritional formulas. Use of exemplary devices disclosed herein may allow a consumer to use less expensive nutritional formulas that do not contain certain lipids and then to add the missing lipids to the formula in a more-digestible form via use of the disclosed devices. For example, rather than purchasing a nutritional formula with the expensive lipids already in it, devices 201, 401 and vessels 501, 601 with a lipid source containing the expensive lipids may be used to introduce a hydrolyzed version of the expensive lipids into the nutritional formula.

Use of devices of the disclosure may decrease the inflammatory response found in the GI tract of a premature infant (or other patient) and/or may condition the GI tract for improved overall absorption of other nutrients, such as, but not limited to, protein and vitamins. The surprising findings may be due to the synergistic effect of pre-hydrolyzing the oils (structured and/or naturally occurring oils, including, but not limited to, DHA and ARA) and/or pre-hydrolyzing fortifiers (including, but not limited to, liquid human-based or non-human-derived fortifiers), as well as their anti-inflammatory effects on the GI tract, thus allowing for better overall GI health.

Figure 13:
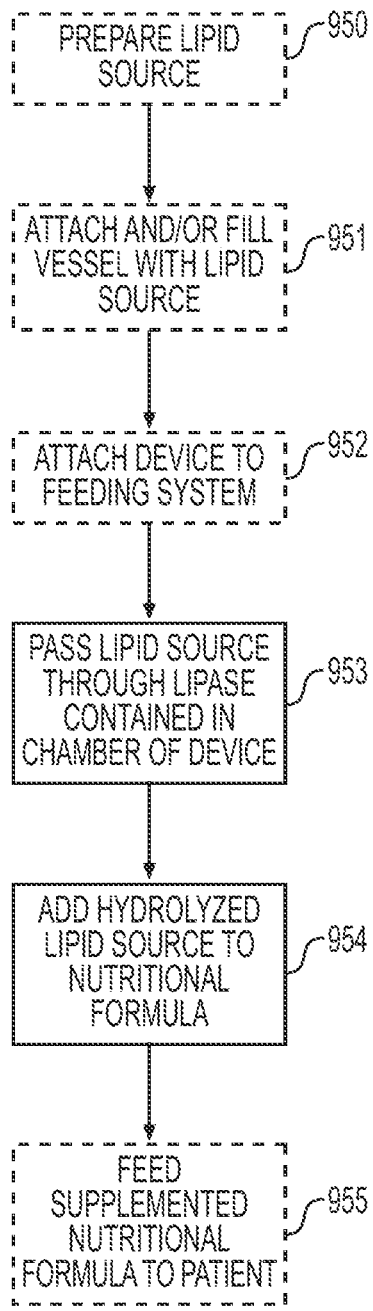
FIG. 13 is a flow chart depicting an exemplary method of using a device, according to embodiments of the present disclosure.

Exemplary devices 201, 401 and vessels 501, 601 may be used in the manner shown in FIG. 13. Those of ordinary skill in the art will recognize that one or more steps of the method depicted in FIG. 13 may be omitted or performed out of the order depicted in FIG. 13, or other steps may also be performed.

The first three steps of the method of FIG. 13 are optional, and, depending on the embodiments of device 201 or device 401 (collectively referred to as 'the device' in reference to FIG. 13), any combination of those steps may be performed, or none of the steps may be performed. First optional step 950 includes preparing a lipid source. As described above, preparing the lipid source may involve mixing, heating, cooling, agitating, or otherwise preparing the lipid source for use in the device. Preparation may occur while the lipid source is already contained in the vessel of the device, preparation may occur prior to introduction of the lipid source into the device, or both. In some embodiments, preparation may include mixing one or more lipids and/or one or more fortifiers together. Additionally, it is recognized that although step 950 is shown as preceding step 951, which precedes 952, it is understood that these steps may be performed in any order.

Step 951 may include attaching the vessel to the lipase chamber (in embodiments in which the vessel is detachable from the device) and/or filling the vessel with the lipid source. In some embodiments, both attaching and filling may occur, while in other embodiments, one (or none) of these may occur. If both actions are taken, the vessel may be filled and then attached to the chamber, while in other embodiments, the vessel may be attached to the chamber and then filled.

At step 952, the device may be attached to a feeding system for adding hydrolyzed lipids to a nutritional formula as the nutritional formula is fed to a patient. For example, the device may be attached to the feeding systems of FIG. 1A or 1B, or may be attached to a feeding system as shown in any of FIGS. 3-9 and described above. Indeed, the device may be attached to or otherwise incorporated in any suitable feeding system.

At step 953, the lipid source of the device may be released from the vessel and passed through the immobilized lipase contained in the chamber of the device. As the lipid source passes through the lipase in the chamber, it reacts with the lipase and is hydrolyzed into monoglycerides and free fatty acids. At step 954, the hydrolyzed lipid source may exit the chamber and may be added to a nutritional formula to supplement the nutritional formula with hydrolyzed lipids. At optional step 955, the supplemented nutritional formula may be fed to a patient either immediately or after some passage of time. The supplemented nutritional formula may be fed to a patient in any suitable manner, for example, via a feeding tube, via a drink (e.g., the hydrolyzed lipids may be added to a beverage), or in any other manner.

While principles of the present disclosure are described herein with reference to illustrative aspects for particular applications, the disclosure is not limited thereto. Those having ordinary skill in the art and access to the teachings provided herein will recognize additional modifications, applications, aspects, and substitution of equivalents that all fall in the scope of the aspects described herein. Accordingly, the present disclosure is not to be considered as limited by the foregoing description.

What is claimed is:

1. A device comprising:
    a vessel including a single opening, wherein the vessel houses a source of lipids;
    a chamber fluidly and directly connected to the opening of the vessel;
    immobilized lipase contained within the chamber and positioned within a flow path in the chamber along which the lipids flow when released from the vessel into the chamber, wherein the opening transitions between retaining or releasing the lipids within the vessel in response to an application of pressure to at least a portion of the device; and
    an outlet through which the lipids flow after passing through the chamber.

2. The device of claim 1, wherein the vessel is removably coupled to the chamber.

3. The device of claim 1, wherein the vessel is compressible.

4. The device of claim 1, further comprising a connector fluidly coupled to the outlet, wherein the connector includes:
    a first opening for receiving a flow of fluid;
    a second opening for outputting the flow of fluid; and
    a connector flow path extending through the connector from the first opening to the second opening.

5. The device of claim 4, further comprising an interface located between the connector and the outlet through which the lipids flow from the outlet and into the connector.

6. The device of claim 5, wherein the interface is removably connected to the connector.

7. The device of claim 1, wherein the lipids include two or more different types of lipids.

8. A device comprising:
a vessel having an opening;
a source of lipids contained within the vessel;
   wherein the opening is configured to transition from a first configuration in which the source of lipids is retained within the vessel, and a second configuration in which the source of lipids is permitted to flow out of the opening in response to an application of pressure to at least a portion of the device,
a chamber coupled to the opening in the vessel;
an output assembly coupled to the chamber;
a flow path extending from the opening in the vessel, through the chamber, and through the output assembly along which the lipids flow through the device when released from the vessel; and
immobilized lipase contained within the chamber and located within the flow path, wherein the lipase is configured to hydrolyze the lipids as the lipids flow through the chamber.

9. The device of claim 8, wherein the vessel includes only one opening.

10. The device of claim 8, wherein the vessel is compressible.

11. The device of claim 8, wherein the output assembly has a first end and a second end, wherein the first end is coupled to the chamber, and the first end has a width that is greater than a width of the second end.

12. The device of claim 8, wherein the output assembly has a first end and a second end, wherein the first end is coupled to the chamber, and the second end has an opening that is covered by a seal when the lipids are contained within the vessel and is uncovered by the seal when the lipids are flowing along the flow path.

13. The device of claim 8, wherein the lipids include two or more different types of lipids.

14. A method of supplementing a nutritional formula with hydrolyzed lipids, the method comprising:
passing a source of lipids stored in a device through a chamber of the device that contains immobilized lipase in order to hydrolyze the lipids by exposing the lipids to the lipase in the chamber, wherein the source of lipids is passed through the chamber in response to an application of pressure to at least a portion of the device;
outputting the hydrolyzed lipids from the chamber of the device; and
adding the hydrolyzed lipids to the nutritional formula;
wherein the nutritional formula is flowed past the device as the hydrolyzed lipids are added to the nutritional formula.

15. The method of claim 14, further comprising preparing the source of lipids prior to passing the lipids through the chamber.

16. The method of claim 15, wherein preparing the source of lipids includes mixing at least two different types of lipids together.

17. The method of claim 14, wherein the source of lipids is stored in a vessel of the device prior to being passed through the chamber, and wherein the method further comprises attaching the vessel to the device prior to passing the source of lipids through the chamber.

18. The method of claim 14, further comprising attaching the device to a feeding system prior to passing the source of lipids through the chamber.

19. The method of claim 18, further comprising feeding the nutritional formula to a subject after the hydrolyzed lipids have been added to the nutritional formula.

20. The method of claim 14, wherein adding the hydrolyzed lipids to the nutritional formula includes outputting the hydrolyzed lipids from the device and into a container containing the nutritional formula.

21. The device of claim 1, wherein the vessel is compressible, and wherein the opening transitions between retaining or releasing the lipids within the vessel in response to compressing the vessel in which the source of lipids is housed.

22. The device of claim 8, wherein the vessel is compressible, and wherein the opening transitions from the first configuration to the second configuration in response to compressing the vessel in which the source of lipids is contained.

23. The method of claim 14, wherein the source of lipids is passed through the chamber in response to compression of the at least a portion of the device.

* * * * *